(12) United States Patent
Viksoe-Nielsen et al.

(10) Patent No.: US 8,021,863 B2
(45) Date of Patent: Sep. 20, 2011

(54) POLYPEPTIDES WITH STARCH DEBRANCHING ACTIVITY

(75) Inventors: Anders Viksoe-Nielsen, Slangerup (DK); Shiro Fukuyama, Chiba (JP); Regine Kopp Behr, Roseville, CA (US); Carsten Andersen, Vaerloese (DK)

(73) Assignees: Novozymes A/S, Bagsvaerd (DE); Novozymes, Inc., Davis, CA (US)

( * ) Notice: Subject to any disclaimer, the term of this patent is extended or adjusted under 35 U.S.C. 154(b) by 604 days.

(21) Appl. No.: 12/032,376

(22) Filed: Feb. 15, 2008

(65) Prior Publication Data

US 2008/0241887 A1    Oct. 2, 2008

Related U.S. Application Data

(60) Provisional application No. 60/890,508, filed on Feb. 19, 2007.

(51) Int. Cl.
*C12P 19/10* (2006.01)
*C12P 19/00* (2006.01)
*C12N 9/00* (2006.01)
*C12N 9/26* (2006.01)

(52) U.S. Cl. ............... 435/102; 435/72; 435/183

(58) Field of Classification Search .............. None
See application file for complete search history.

(56) References Cited

U.S. PATENT DOCUMENTS 7,618,795 B2 * 11/2009 Vikso-Nielsen et al. ....... 435/41

FOREIGN PATENT DOCUMENTS

| EP | 1200552 | 11/2005 |
|---|---|---|
| WO | WO 98/16633 | 4/1998 |
| WO | WO 00/01796 | 1/2000 |
| WO | WO 2005/003311 | 1/2005 |
| WO | WO 2005/045018 | 5/2005 |
| WO | WO 2005/096804 | 10/2005 |
| WO | WO 2006/066596 | 6/2006 |

OTHER PUBLICATIONS

Van Bueren et al., "x-Glucan recognition by a new family of carbohydrate-binding modules found primarily in bacterial pathogens", Biochemistry, vol. 43, pp. 15633-15642 (2004).

N. Sauvonet et al., "Extracellular secretion of pullulanase is unaffected by minor sequence changes but is usually prevented by adding reporter proteins to its n- or c-terminal end", Journal of Bacteriology, vol. 177, No. 18, pp. 5238-5246 (1995).

Boraston et al., "Carbohydrate-binding modules: fine-tuning polysaccharide recognition", Biochem. J., vol. 382, pp. 769-781 (2004).

Kelly et al., "Molecular genetic analysis of the pullulanase B gene of *Bacillus acidopullulyticus*", FEMS Microbiology Letters, vol. 115, pp. 97-106 (1994).

* cited by examiner

*Primary Examiner* — Tekchand Saidha
*Assistant Examiner* — Younus Meah
(74) *Attorney, Agent, or Firm* — Elias Lambiris

(57) ABSTRACT

Polypeptides comprising a catalytic starch debranching domain and a starch binding domain are disclosed. The polypeptides comprising the starch binding domain have an improved functionality in raw starch degradation compared with same catalytic unit in same amount but without the starch binding domain.

16 Claims, 16 Drawing Sheets

SEQUENCE LISTING

<160> NUMBER OF SEQ ID NOS: 15

<210> SEQ ID NO 1
<211> LENGTH: 8
<212> TYPE: PRT
<213> ORGANISM: Artificial Sequence
<220> FEATURE:
<223> OTHER INFORMATION: Synthetic

<400> SEQUENCE: 1

Pro Glu Pro Thr Pro Glu Pro Asn
1               5

<210> SEQ ID NO 2
<211> LENGTH: 37
<212> TYPE: DNA
<213> ORGANISM: Artificial Sequence
<220> FEATURE:
<223> OTHER INFORMATION: Primer

<400> SEQUENCE: 2
ccaggcctta agggccgcat gcgtccttct ttgtgct        37

<210> SEQ ID NO 3
<211> LENGTH: 27
<212> TYPE: DNA
<213> ORGANISM: Artificial Sequence
<220> FEATURE:
<223> OTHER INFORMATION: Primer

<400> SEQUENCE: 3
gagctccttt caatgtgata catatga                   27

```
<210> SEQ ID NO 4
<211> LENGTH: 26
<212> TYPE: DNA
<213> ORGANISM: Artificial Sequence
<220> FEATURE:
<223> OTHER INFORMATION: Primer

<400> SEQUENCE: 4
gtcgaccgcg tataataaag aataat                                          26

<210> SEQ ID NO 5
<211> LENGTH: 30
<212> TYPE: DNA
<213> ORGANISM: Artificial Sequence
<220> FEATURE:
<223> OTHER INFORMATION: Primer

<400> SEQUENCE: 5
ggcccttaag gcccactaat attaataaac                                      30

<210> SEQ ID NO 6
<211> LENGTH: 50
<212> TYPE: DNA
<213> ORGANISM: Artificial Sequence
<220> FEATURE:
<223> OTHER INFORMATION: Primer

<400> SEQUENCE: 6
gagctctata aaatgagga gggaaccgaa tgtccctaat acgttctagg                 50

<210> SEQ ID NO 7
<211> LENGTH: 27
<212> TYPE: DNA
<213> ORGANISM: Artificial Sequence
<220> FEATURE:
<223> OTHER INFORMATION: Primer

<400> SEQUENCE: 7
acgcgtttaa ttttgatcaa tgacatc                                         27

<210> SEQ ID NO 8
<211> LENGTH: 38
<212> TYPE: DNA
<213> ORGANISM: Artificial Sequence
<220> FEATURE:
<223> OTHER INFORMATION: Primer

<400> SEQUENCE: 8
agcgcaagta atccgaacga tacacaagca gatcgaat                             38

<210> SEQ ID NO 9
<211> LENGTH: 38
<212> TYPE: DNA
<213> ORGANISM: Artificial Sequence
<220> FEATURE:
<223> OTHER INFORMATION: Primer

<400> SEQUENCE: 9
tcggttccgg attttgatca atgacatctt cagatgta                             38

<210> SEQ ID NO 10
<211> LENGTH: 38
<212> TYPE: DNA
<213> ORGANISM: Artificial Sequence
<220> FEATURE:
<223> OTHER INFORMATION: Primer

<400> SEQUENCE: 10
```

```
ccggaaccga ccccggaacc gaacacttcc caaataac                               38

<210> SEQ ID NO 11
<211> LENGTH: 38
<212> TYPE: DNA
<213> ORGANISM: Artificial Sequence
<220> FEATURE:
<223> OTHER INFORMATION: Primer

<400> SEQUENCE: 11
aaggagataa aagcatgtcg aactggtact ggctgtat                              38

<210> SEQ ID NO 12
<211> LENGTH: 1103
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(885)

<400> SEQUENCE: 12 agc gca agt aat ccg aac gat aca caa gca gat cga att aag atg gat      48
Ser Ala Ser Asn Pro Asn Asp Thr Gln Ala Asp Arg Ile Lys Met Asp
  1               5                  10                  15 gaa ttg gct caa gct gtg gta ttt act tca caa ggg gta cca ttt atg      96
Glu Leu Ala Gln Ala Val Val Phe Thr Ser Gln Gly Val Pro Phe Met
             20                  25                  30 caa ggt gga gaa gaa atg ctg cgg aca aaa ggc ggt aat gat aat agt     144
Gln Gly Gly Glu Glu Met Leu Arg Thr Lys Gly Gly Asn Asp Asn Ser
         35                  40                  45 tac aat gcc ggg gat agc gtg aat cag ttc gat tgg tca aga aaa gca     192
Tyr Asn Ala Gly Asp Ser Val Asn Gln Phe Asp Trp Ser Arg Lys Ala
     50                  55                  60 caa ttt gaa aat gta ttc gac tac tat tct tgg ttg att cat cta cgt     240
Gln Phe Glu Asn Val Phe Asp Tyr Tyr Ser Trp Leu Ile His Leu Arg
 65                  70                  75                  80 gat aat cac cca gca ttc cgt atg acg aca gcg gat caa atc aaa caa     288
Asp Asn His Pro Ala Phe Arg Met Thr Thr Ala Asp Gln Ile Lys Gln
                 85                  90                  95 aat ctc act ttc ttg gat agc cca acg aac act gta gca ttt gaa tta     336
Asn Leu Thr Phe Leu Asp Ser Pro Thr Asn Thr Val Ala Phe Glu Leu
            100                 105                 110 aaa aat cat gcc aat cat gat aaa tgg aaa aac att ata gtt atg tat     384
Lys Asn His Ala Asn His Asp Lys Trp Lys Asn Ile Ile Val Met Tyr
        115                 120                 125 aat cca aat aaa act gca caa act ctc act cta cca agt gga aat tgg     432
Asn Pro Asn Lys Thr Ala Gln Thr Leu Thr Leu Pro Ser Gly Asn Trp
    130                 135                 140 aca att gta gga tta ggc aat caa gta ggt gag aaa tca cta ggc cat     480
Thr Ile Val Gly Leu Gly Asn Gln Val Gly Glu Lys Ser Leu Gly His
145                 150                 155                 160 gta aat ggc acg gtt gag gtg cca gct ctt agt acg atc att ctt cat     528
Val Asn Gly Thr Val Glu Val Pro Ala Leu Ser Thr Ile Ile Leu His
                165                 170                 175 cag ggt aca tct gaa gat gtc att gat caa aat ccg gaa ccg acc ccg     576
Gln Gly Thr Ser Glu Asp Val Ile Asp Gln Asn Pro Glu Pro Thr Pro
            180                 185                 190 gaa ccg aac act tcc caa ata aca ttt act gta aat aac gcc aca acc     624
Glu Pro Asn Thr Ser Gln Ile Thr Phe Thr Val Asn Asn Ala Thr Thr
        195                 200                 205
```

```
gtt tgg gga caa aat gta tac gtt gtc ggg aat att tcg cag ctg ggg    672
Val Trp Gly Gln Asn Val Tyr Val Val Gly Asn Ile Ser Gln Leu Gly
    210                 215                 220 aac tgg gat cca gtc cac gca gtt caa atg acg ccg tct tct tat cca    720
Asn Trp Asp Pro Val His Ala Val Gln Met Thr Pro Ser Ser Tyr Pro
225                 230                 235                 240 aca tgg act gta aca atc cct ctt ctt caa ggg caa aac ata caa ttt    768
Thr Trp Thr Val Thr Ile Pro Leu Leu Gln Gly Gln Asn Ile Gln Phe
                245                 250                 255 aaa ttt atc aaa aaa gat tca gct gga aat gtc att tgg gaa gat ata    816
Lys Phe Ile Lys Lys Asp Ser Ala Gly Asn Val Ile Trp Glu Asp Ile
                260                 265                 270 tcg aat cga aca tac acc gtc cca act gct gca tcc gga gca tat aca    864
Ser Asn Arg Thr Tyr Thr Val Pro Thr Ala Ala Ser Gly Ala Tyr Thr
            275                 280                 285 gcc agc tgg aac gtg ccc tag acgcgttaat caataaaaaa acgctgtgcg       915
Ala Ser Trp Asn Val Pro
        290 gttaagggc acagcgtttt tttgtgtatg gatccgcggc cgcgcgtcaa caatgacctt    975
tatgccatat tcttcagcgg ctgcacacat ttctttaaat tcttgttcag tacctaagta  1035
acggttgcca atttgatacg atgtcggctg atacagccag taccagttcg acatgctttt  1095
atctcctt                                                          1103

<210> SEQ ID NO 13
<211> LENGTH: 294
<212> TYPE: PRT
<213> ORGANISM: Artificial Sequence
<220> FEATURE:
<223> OTHER INFORMATION: Synthetic Construct

<400> SEQUENCE: 13

Ser Ala Ser Asn Pro Asn Asp Thr Gln Ala Asp Arg Ile Lys Met Asp
1               5                   10                  15

Glu Leu Ala Gln Ala Val Val Phe Thr Ser Gln Gly Val Pro Phe Met
            20                  25                  30

Gln Gly Gly Glu Glu Met Leu Arg Thr Lys Gly Gly Asn Asp Asn Ser
        35                  40                  45

Tyr Asn Ala Gly Asp Ser Val Asn Gln Phe Asp Trp Ser Arg Lys Ala
    50                  55                  60

Gln Phe Glu Asn Val Phe Asp Tyr Tyr Ser Trp Leu Ile His Leu Arg
65                  70                  75                  80

Asp Asn His Pro Ala Phe Arg Met Thr Thr Ala Asp Gln Ile Lys Gln
                85                  90                  95

Asn Leu Thr Phe Leu Asp Ser Pro Thr Asn Thr Val Ala Phe Glu Leu
            100                 105                 110

Lys Asn His Ala Asn His Asp Lys Trp Lys Asn Ile Ile Val Met Tyr
        115                 120                 125

Asn Pro Asn Lys Thr Ala Gln Thr Leu Thr Leu Pro Ser Gly Asn Trp
    130                 135                 140

Thr Ile Val Gly Leu Gly Asn Gln Val Gly Glu Lys Ser Leu Gly His
145                 150                 155                 160

Val Asn Gly Thr Val Glu Val Pro Ala Leu Ser Thr Ile Leu His
                165                 170                 175

Gln Gly Thr Ser Glu Asp Val Ile Asp Gln Asn Pro Glu Pro Thr Pro
            180                 185                 190

Glu Pro Asn Thr Ser Gln Ile Thr Phe Thr Val Asn Asn Ala Thr Thr
        195                 200                 205
```

```
Val Trp Gly Gln Asn Val Tyr Val Gly Asn Ile Ser Gln Leu Gly
    210                 215                 220

Asn Trp Asp Pro Val His Ala Val Gln Met Thr Pro Ser Ser Tyr Pro
225                 230                 235                 240

Thr Trp Thr Val Thr Ile Pro Leu Leu Gln Gly Gln Asn Ile Gln Phe
                245                 250                 255

Lys Phe Ile Lys Lys Asp Ser Ala Gly Asn Val Ile Trp Glu Asp Ile
                260                 265                 270

Ser Asn Arg Thr Tyr Thr Val Pro Thr Ala Ala Ser Gly Ala Tyr Thr
            275                 280                 285

Ala Ser Trp Asn Val Pro
    290
```

```
<210> SEQ ID NO 14
<211> LENGTH: 969
<212> TYPE: PRT
<213> ORGANISM: Artificial Sequence
<220> FEATURE:
<223> OTHER INFORMATION: Synthetic
<220> FEATURE:
<221> NAME/KEY: SIGNAL
<222> LOCATION: (1)..(33)
<220> FEATURE:
<221> NAME/KEY: mat_peptide
<222> LOCATION: (34)..(969)

<400> SEQUENCE: 14

Met Ser Leu Ile Arg Ser Arg Tyr Asn His Phe Val Ile Leu Phe Thr
                -30                 -25                 -20

Val Ala Ile Met Phe Leu Thr Val Cys Phe Pro Ala Tyr Lys Ala Leu
        -15                 -10                 -5

Ala Asp Ser Thr Ser Thr Glu Val Ile Val His Tyr His Arg Phe Asp
 -1  1               5                  10                  15

Ser Asn Tyr Ala Asn Trp Asp Leu Trp Met Trp Pro Tyr Gln Pro Val
                20                  25                  30

Asn Gly Asn Gly Ala Ala Tyr Glu Phe Ser Gly Lys Asp Asp Phe Gly
            35                  40                  45

Val Lys Ala Asp Val Gln Val Pro Gly Asp Asp Thr Gln Val Gly Leu
        50                  55                  60

Ile Val Arg Thr Asn Asp Trp Ser Gln Lys Asn Thr Ser Asp Asp Leu
    65                  70                  75

His Ile Asp Leu Thr Lys Gly His Glu Ile Trp Ile Val Gln Gly Asp
80                  85                  90                  95

Pro Asn Ile Tyr Tyr Asn Leu Ser Asp Ala Gln Ala Ala Ala Thr Pro
                100                 105                 110

Lys Val Ser Asn Ala Tyr Leu Asp Asn Glu Lys Thr Val Leu Ala Lys
            115                 120                 125

Leu Thr Asn Pro Met Thr Leu Ser Asp Gly Ser Ser Gly Phe Thr Val
        130                 135                 140

Thr Asp Lys Thr Thr Gly Glu Gln Ile Pro Val Thr Ala Ala Thr Asn
    145                 150                 155

Ala Asn Ser Ala Ser Ser Glu Gln Thr Asp Leu Val Gln Leu Thr
160                 165                 170                 175

Leu Ala Ser Ala Pro Asp Val Ser His Thr Ile Gln Val Gly Ala Ala
                180                 185                 190

Gly Tyr Glu Ala Val Asn Leu Ile Pro Arg Asn Val Leu Asn Leu Pro
            195                 200                 205
```

```
Arg Tyr Tyr Tyr Ser Gly Asn Asp Leu Gly Asn Val Tyr Ser Asn Lys
            210                 215                 220
Ala Thr Ala Phe Arg Val Trp Ala Pro Thr Ala Ser Asp Val Gln Leu
225                 230                 235
Leu Leu Tyr Asn Ser Glu Thr Gly Pro Val Thr Lys Gln Leu Glu Met
240                 245                 250                 255
Gln Lys Ser Asp Asn Gly Thr Trp Lys Leu Lys Val Pro Gly Asn Leu
                260                 265                 270
Lys Asn Trp Tyr Tyr Leu Tyr Gln Val Thr Val Asn Gly Lys Thr Gln
                275                 280                 285
Thr Ala Val Asp Pro Tyr Val Arg Ala Ile Ser Val Asn Ala Thr Arg
            290                 295                 300
Gly Met Ile Val Asp Leu Glu Asp Thr Asn Pro Pro Gly Trp Lys Glu
305                 310                 315
Asp His Gln Gln Thr Pro Ala Asn Pro Val Asp Glu Val Ile Tyr Glu
320                 325                 330                 335
Val His Val Arg Asp Phe Ser Ile Asp Ala Asn Ser Gly Met Lys Asn
                340                 345                 350
Lys Gly Lys Tyr Leu Ala Phe Thr Glu His Gly Thr Lys Gly Pro Asp
                355                 360                 365
Asn Val Lys Thr Gly Ile Asp Ser Leu Lys Glu Leu Gly Ile Asn Ala
            370                 375                 380
Val Gln Leu Gln Pro Ile Glu Glu Phe Asn Ser Ile Asp Glu Thr Gln
385                 390                 395
Pro Asn Met Tyr Asn Trp Gly Tyr Asp Pro Arg Asn Tyr Asn Val Pro
400                 405                 410                 415
Glu Gly Ala Tyr Ala Thr Thr Pro Glu Gly Thr Ala Arg Ile Thr Gln
                420                 425                 430
Leu Lys Gln Leu Ile Gln Ser Ile His Lys Asp Arg Ile Ala Ile Asn
            435                 440                 445
Met Asp Val Val Tyr Asn His Thr Phe Asn Val Gly Val Ser Asp Phe
            450                 455                 460
Asp Lys Ile Val Pro Gln Tyr Tyr Tyr Arg Thr Asp Ser Ala Gly Asn
465                 470                 475
Tyr Thr Asn Gly Ser Gly Val Gly Asn Glu Ile Ala Thr Glu Arg Pro
480                 485                 490                 495
Met Val Gln Lys Phe Val Leu Asp Ser Val Lys Tyr Trp Val Lys Glu
                500                 505                 510
Tyr His Ile Asp Gly Phe Arg Phe Asp Leu Met Ala Leu Leu Gly Lys
            515                 520                 525
Asp Thr Met Ala Lys Ile Ser Lys Glu Leu His Ala Ile Asn Pro Gly
            530                 535                 540
Ile Val Leu Tyr Gly Glu Pro Trp Thr Gly Gly Thr Ser Gly Leu Ser
    545                 550                 555
Ser Asp Gln Leu Val Thr Lys Gly Gln Gln Lys Gly Leu Gly Ile Gly
560                 565                 570                 575
Val Phe Asn Asp Asn Ile Arg Asn Gly Leu Asp Gly Asn Val Phe Asp
                580                 585                 590
Lys Ser Ala Gln Gly Phe Ala Thr Gly Asp Pro Asn Gln Val Asn Val
            595                 600                 605
Ile Lys Asn Gly Val Met Gly Ser Ile Ser Asp Phe Thr Ser Ala Pro
        610                 615                 620
Ser Glu Thr Ile Asn Tyr Val Ser His Asp Asn Met Thr Leu Trp
625                 630                 635
```

```
Asp Lys Ile Ser Ala Ser Asn Pro Asn Asp Thr Gln Ala Asp Arg Ile
640                 645                 650                 655

Lys Met Asp Glu Leu Ala Gln Ala Val Val Phe Thr Ser Gln Gly Val
            660                 665                 670

Pro Phe Met Gln Gly Gly Glu Met Leu Arg Thr Lys Gly Gly Asn
            675                 680                 685

Asp Asn Ser Tyr Asn Ala Gly Asp Ser Val Asn Gln Phe Asp Trp Ser
            690                 695                 700

Arg Lys Ala Gln Phe Glu Asn Val Phe Asp Tyr Tyr Ser Trp Leu Ile
        705                 710                 715

His Leu Arg Asp Asn His Pro Ala Phe Arg Met Thr Thr Ala Asp Gln
720                 725                 730                 735

Ile Lys Gln Asn Leu Thr Phe Leu Asp Ser Pro Thr Asn Thr Val Ala
                740                 745                 750

Phe Glu Leu Lys Asn His Ala Asn His Asp Lys Trp Lys Asn Ile Ile
            755                 760                 765

Val Met Tyr Asn Pro Asn Lys Thr Ala Gln Thr Leu Thr Leu Pro Ser
            770                 775                 780

Gly Asn Trp Thr Ile Val Gly Leu Gly Asn Gln Val Gly Glu Lys Ser
785                 790                 795

Leu Gly His Val Asn Gly Thr Val Glu Val Pro Ala Leu Ser Thr Ile
800                 805                 810                 815

Ile Leu His Gln Gly Thr Ser Glu Asp Val Ile Asp Gln Asn Pro Glu
                820                 825                 830

Pro Thr Pro Glu Pro Asn Thr Ser Gln Ile Thr Phe Thr Val Asn Asn
            835                 840                 845

Ala Thr Thr Val Trp Gly Gln Asn Val Tyr Val Val Gly Asn Ile Ser
        850                 855                 860

Gln Leu Gly Asn Trp Asp Pro Val His Ala Val Gln Met Thr Pro Ser
    865                 870                 875

Ser Tyr Pro Thr Trp Thr Val Thr Ile Pro Leu Leu Gln Gly Gln Asn
880                 885                 890                 895

Ile Gln Phe Lys Phe Ile Lys Lys Asp Ser Ala Gly Asn Val Ile Trp
                900                 905                 910

Glu Asp Ile Ser Asn Arg Thr Tyr Thr Val Pro Thr Ala Ala Ser Gly
            915                 920                 925

Ala Tyr Thr Ala Ser Trp Asn Val Pro
        930                 935

<210> SEQ ID NO 15
<211> LENGTH: 102
<212> TYPE: PRT
<213> ORGANISM: Thermoanaerobacter sp.

<400> SEQUENCE: 15

Thr Gly Asn Gln Val Cys Val Arg Phe Val Val Asn Asn Ala Thr Thr
1               5                   10                  15

Val Trp Gly Glu Asn Val Tyr Leu Thr Gly Asn Val Ala Glu Leu Gly
            20                  25                  30

Asn Trp Asp Thr Ser Lys Ala Ile Gly Pro Met Phe Asn Gln Val Val
        35                  40                  45

Tyr Gln Tyr Pro Thr Trp Tyr Tyr Asp Val Ser Val Pro Ala Gly Thr
    50                  55                  60

Thr Ile Glu Phe Ile Lys Lys Asn Gly Ser Thr Val Thr Trp Glu Gly
65                  70                  75                  80
```

```
Gly Tyr Asn His Val Tyr Thr Thr Pro Thr Ser Gly Thr Ala Thr Val
                85                  90                  95

Ile Val Asp Trp Gln Pro
            100
```

POLYPEPTIDES WITH STARCH DEBRANCHING ACTIVITY

CROSS-REFERENCE TO RELATED APPLICATIONS

Figure 1:
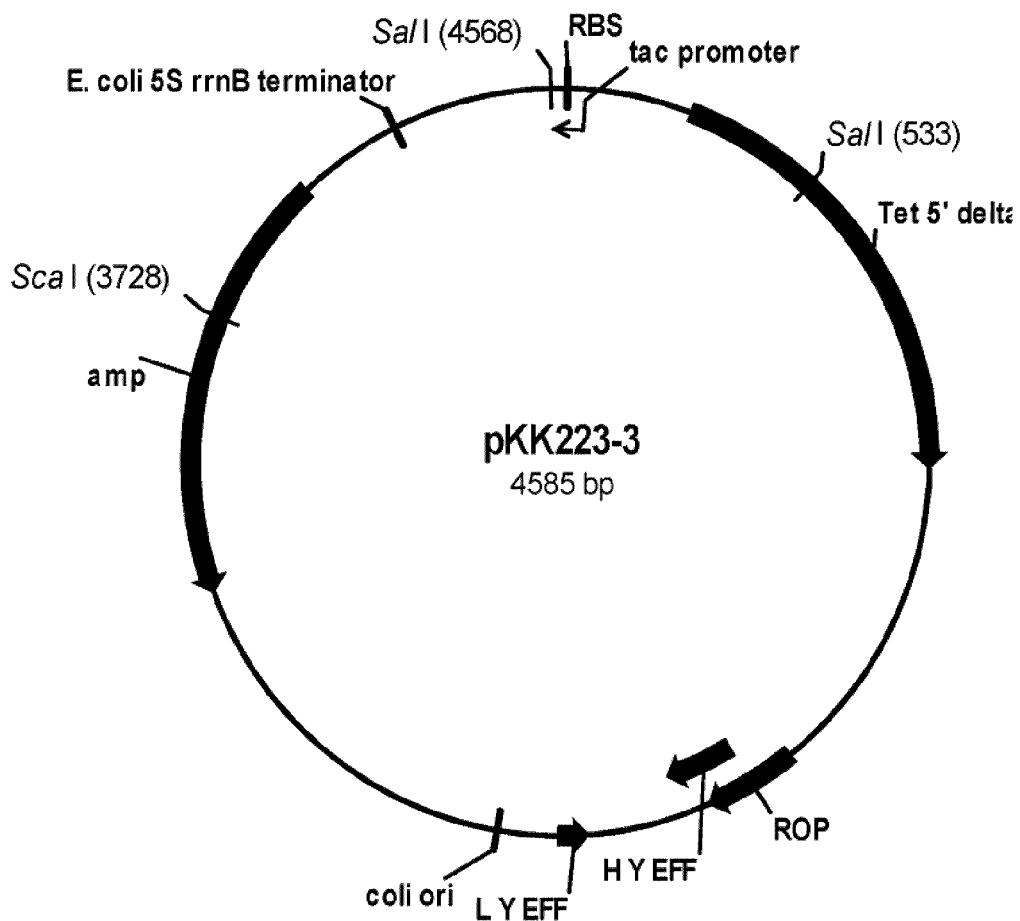

This application claims priority or the benefit under 35 U.S.C. 119 of U.S. Provisional Application No. 60/890,508 filed Feb. 19, 2007, the contents of which are fully incorporated herein by reference.

FIELD OF THE INVENTION

The invention relates to polypeptides with starch debranching activity and to their use in starch hydrolysis, in particular in raw starch hydrolysis.

BACKGROUND FOR THE INVENTION

Starch is a natural storage carbohydrate found in a large variety of plants. Starch containing crops are important agricultural crops in almost every part of the world. Among the most important crops containing starch can be mentioned corn, wheat, rice, barley and potatoes.

Enzymatic degradation of starch is part of many industrial processes including brewing, production of glucose or high fructose syrups and production of drinking or fuel ethanol.

In its natural state starch is quite resistant against degradation by many enzymes, and therefore industrial enzymatic degradation of starch is traditionally initiated by a heating step where starch is gelatinized, which renders the starch more sensitive to many enzymes. Gelatinization leads to a high increase in viscosity which may give technical difficulties but is usually necessary in order to obtain a satisfactory high degree of degradation.

A combination of endo-acting enzymes, e.g. α-amylase; exo-acting enzymes, e.g. β-amylase and glucoamylase; and debranching enzymes; e.g. pullulanases and iso-amylases are used for enzymatic degradation of starch.

WO 98/16633 describes hybrids comprising a starch degrading enzyme, a carbohydrate binding domain (CBD) and a linker. Pullulanase is mentioned as an example of a starch degrading enzyme. The only exemplified hybrid consists of an alpha-amylase a CBD and a linker.

EP 1200552 B1 discloses the expression in plants of starch altering proteins, e.g. pullulanases, as hybrids with a starch binding domain (SBD). The hybrids have the benefit that they are localized to the starch granules in the plants and thereby altered starch is produced.

Van Bueren et al. Biochemistry 2004, 43: 15633-15642 describe a four module protein having pullulanase activity isolated from the hyperthermophile eubacteria *Thermotoga maritima*. One of the four modules of the protein was identifies as a new type carbohydrate binding domain having highest affinity for alpha-(1-4) linked glucans.

N. Sauvonnet et al. 1995. J. Bact. 177 (18): 5238-5246, disclose a study relating to a bacterial pullulanase where it was found that minor insertions could be accepted, fusions of larger proteins to the N- or C-terminal could usually not be secreted efficiently.

WO 2005/096804 discloses polynucleotides for expression in plants. The polynucleotide may encode a fusion polypeptide comprising a first polypeptide and a second peptide. The first polypeptide may have pullulanase activity, and the second peptide may be an N-terminal signal sequence from a starch binding domain.

SUMMARY OF THE INVENTION

The inventors have found that by adding a starch binding domain (SBD) onto a starch debranching domain, it is possible to obtain a better raw starch hydrolysis.

Accordingly, the invention provides a fusion polypeptide (hybrid polypeptide) comprising a catalytic starch debranching domain, a starch binding domain (SBD) and optionally a linker connecting the domains. The catalytic starch debranching domain is preferably a pullulanase.

The invention also provides the preparation of the fusion polypeptide according to the invention. The invention further provides the use of a polypeptide comprising a catalytic starch debranching domain and a starch binding domain in starch degradation, in particular raw starch degradation.

SHORT DESCRIPTION OF THE DRAWINGS

FIGS. 1-16 show the plasmids pKK223-3, pNBT51, pNBT52, pNBT53, pNBT54, pNBT35, pNBT30, pNBT31, pNBT36, pRB165, pMRT135, pWWi006, pMDT105, pMDT114, pMBin115 and pRB212. Details are given in the Examples.

DEFINITIONS

A domain of a polypeptide is according to the invention intended to mean a part of a polypeptide being structurally and/or functionally distinct of the reminder of the polypeptide. For example polypeptides are known having a catalytic domain responsible for the catalytic properties of the polypeptide, while a second domain may be responsible for binding to a particular structural component. Natural polypeptides may consist of only one domain or may comprise two or more domains. Typically each domain is capable of folding and functioning independently of the reminder of the polypeptide.

A catalytic domain may be a part of an enzyme or it may be the complete enzyme.

A starch debranching enzyme is according to the invention intended to mean an enzyme capable of catalyzing the debranching of starch.

Starch is a polymer composed of glucosyl residues connected via α-1,4 bonds. Generally starch is composed of amylose, a polymer consisting of glucosyl residues connected via α-1,4 linkages, and amylopectin also consisting of glucosyl residues connected via α-1,4 linkages with branches of α-1,4 linked glucosyl chains connected to another α-1,4 linked glucosyl chains via an α-1,6 linkage. Debranching enzymes which can attack amylopectin include isoamylases (E.C. 3.2.1.68) and pullulanases (E.C. 3.2.1.41). Isoamylases hydrolyses α-1,6-D-glucosidic branch linkages in amylopectin and β-limit dextrins and can be distinguished from pullulanases by the inability of isoamylase to attack pullulan, and by their limited action on α-limit dextrins. The ratio of amylose to amylopectin, the frequency of branches on the amylopectin and the average chain length for the branches varies considerably depending on the source of the starch but this is not considered important for the present invention. Thus a starch debranching enzyme is a polypeptide capable of catalyzing the degradation of the α-1,6 linkages in amylopectin and thereby removing branches from an amylopectin structure.

In the present specification the term "starch debranching enzyme" or grammatically equivalent similar expressions are intended to mean an enzyme or protein domain having catalytic activity being capable of degrading an α-1,6-glucosidic linkage connecting two glucose units. Thus the term includes but is not limited to enzymes described as pullulanases or iso-amylases.

The starch debranching enzyme may be a protein as found in nature, a fragment of a protein found in nature or it may be a variant of such a protein.

With the term variant is understood a protein directly or indirectly derived from a natural protein by at least one alteration, such as a substitution, insertion or deletion. Variants of a protein may be prepared using techniques well known to the skilled person within molecular biology and described in established handbooks such as J. Sambrook, E. F. Fritsch, and T. Maniatis, 1989, *Molecular Cloning, A Laboratory Manual*, 2d edition, Cold Spring Harbor, N.Y.

A catalytic starch debranching domain is intended to mean a part of starch debranching enzyme, which part is responsible for the catalytic activity of the complete enzyme. Thus a catalytic starch debranching domain may the complete or a part of a starch debranching enzyme.

Carbohydrate binding domains are protein structures capable of binding a carbohydrate, usually with non-covalent bindings. Carbohydrate binding domains includes domains binding polysaccharides such as cellulose, xylan or starch. Several carbohydrate binding domains have been described in the literature, and have been grouped in families, for review see Boraston et al. (2004) Biochem. J. 382: 769-781 and http://afmb.cnrs-mrs.fr/CAZY/index.html for the grouping of CBM families.

A starch binding domain is a carbohydrate binding domain having specificity for starch, in particular raw starch. Starch binding domains are found in at least the carbohydrate binding domain families CBM-20, CBM-21, CBM-25, CBM-26, CBM-34, CBM-41 and CBM-45.

A linker is a proteinaceous part separating the catalytic starch debranching domain from the carbohydrate binding domain without interfering with the activity of the two domains.

Starch degradation is in the present specification understood as the enzymatic depolymerization of starch forming dextrins and glucose. Starch degradation is usually performed using a combination of enzymes capable of hydrolyzing α-1,4 and α-1,6 glucosidic bonds such as α-amylases, β-amylases, glucoamylases, pullulanases, iso-amylases and CGTases. Usually starch degradation is performed using a combination of at least one endo-acting amylase, such as an α-amylase, and at least one exo-acting amylase, such as a β-amylase or a glucoamylase, and optionally a debranching enzyme such as a pullulanase. Traditionally starch degradation is performed by heating a mixture of starch containing material and water followed by the addition of the enzymes and holding the mixture at a suitable temperature until the degradation is completed or reached a desirable extend. During the initial heating of the mixture of starch containing material and water the starch will gelatinize leading to a significant increase in the viscosity of the mixture.

Raw starch is in the present specification understood as non gelatinized starch. Raw starch degradation is a starch degradation process performed without starch gelatinization and the following substantial increase of viscosity.

DETAILED DESCRIPTION OF THE INVENTION

The invention provides a fusion polypeptide comprising a starch debranching catalytic domain and a starch binding domain and optionally a linker sequence connecting said domains.

Starch Debranching Catalytic Domain

The starch debranching catalytic domain may in principle be any such domain capable of catalyzing the debranching of starch. The starch debranching catalytic domain is preferably derived from a pullulanase.

Debranching enzymes have been described from several organisms mainly bacteria including species of the genus *Bacillus* and *Pyrococcus*; and plants including barley and rice. For the present invention it is preferred that the debranching enzyme is derived from a bacterium, such as a pullulanase derived from *Bacillus acidopullulyticus, B. deramificans, Klebsiella pneumonia, K. aerogenes* or *Pyrococcus* sp.; or an isoamylase derived from *Rhodothermus marinus, Pseudomonas amytoderamosa, Pseudomonas* sp. SMP1, *Flavobacterium odoratum, Sullolobus acidocaldarius* or *S. solfatarius*.

Preferably is the debranching enzyme according to the invention a pullulanase derived from a bacterium, preferably from the genus *Bacillus*.

In a preferred embodiment the debranching enzyme is a pullulanase derived from *B. acidopullulyticus*, in particular pulB/C hybrid (fusion) consisting of residues 11-837 of SEQ ID NO: 14. It consists of the portion of the pulB gene upstream of the Bam HI site within the coding region (see Kelly et al., 1994 FEMS Microbiol. Letters, 115: 97-106; incorporated by reference) and the portion of the pulC gene of *B. acidopullulyticus* downstream of the Bam HI site within the coding region.

The debranching enzyme may be a natural enzyme or it may be a variant of a natural enzyme still having debranching activity. In this connection a variant is understood as a polypeptide differing from a natural polypeptide by at least one amino acid residue. The at least one differing amino acid may be selected among substitutions, insertion or deletions of one or more amino acid residue or any combination thereof. Methods for preparing such variants are well known to the skilled person.

In one embodiment is the debranching enzyme a variant as disclosed in WO 00/01796 or WO 01/51620, both incorporated herein by reference.

Starch Binding Domain (SBD)

The starch binding domain (SBD) may in principle be any protein domain capable of binding to starch. Preferably the SBD is capable of binding to raw starch, which in this specification is understood as non gelatinized starch.

The SBD may belong to a recognized group of carbohydrate binding modules, or it may have a unique structure not being similar to other known carbohydrate binding modules.

Several carbohydrate binding modules (CBMs) have been described in the literature and grouped in families based on sequence and structural similarities. Starch binding domains are found in the carbohydrate binding domain families CBM-20, CBM-21, CBM-25, CBM-26, CBM-34, CBM-41 and CBM-45. It is preferred that the SBD according to the invention belongs to the CBM-20 family.

SBDs belonging to the CBM-20 family have been found in enzymes derived from archaebacteria such as in the PF1108 protein from *Pyrococcus furiosus* DSM 3638 (Uniprot acc. No. Q8U1U7); from eubacteria such as in the α-amylase protein derived from *Anoxybacillus contaminans* (previously known as *Bacillus flavothermus*), the α-amylase from *Bacillus licheniformis* and the α-amylase from *Bacillus circulans* AM7; and from eukaryotes such as in the glucoamylase from *Aspergillus niger*.

According to the invention it is preferred that the SBD belonging to the CBM-20 family is preferably derived from a microorganism belonging to the genus, *Bacillus, Geobacillus, Anoxybacillus, Pyrococcus* or *Aspergillus*.

Two SBDs belonging to the CBM-20 family are shown in SEQ ID NO: 15 and as residues 838-936 of SEQ ID NO: 14. The former is derived from the *Thermoanaerobacter* sp. CGTase (Joergensen et al (1997) in Biotechnol. Lett. 19:1027-1031), and the latter is derived from *Anoxybacillus contaminans* α-amylase (WO 2006/066596).

The SBD may be a natural SBD or it may be a variant of a natural SBD having starch binding activity. In this connection a variant is understood as a polypeptide differing from a natural polypeptide by at least one amino acid residue. The at least one differing amino acid may be selected among substitutions, insertion or deletions of one or more amino acid residue or any combination thereof. Methods for preparing variant of a protein such as a SBD are well known to the skilled person.

Linker

An important purpose of the linker is separating the catalytic domain from the SBD in order to prevent any steric hindrance of the function of one domain of the fusion by another part of the fusion. The linker may consist of only one or a few amino acids resulting of the construction strategy of the fusion, or the linker may be a longer peptide. In principle there is no upper length of the linker but for practically reasons A is preferred that the linker is not longer than approximately 100 amino acid residues. Thus a preferred linker according to the invention is between 1 and 100 amino acids preferably between 2 and 50 amino acids, more preferred between 2 and 25 amino acids, and most preferred between 5 and 20 amino acids.

The exact sequence of the linker is not critical, however it is preferred that the sequence of the linker is selected so that the linker does not adopt any rigid structure. The amino acid composition of the linker is preferably selected so that the linker is rich in hydrophilic residues. Further proline residues may be beneficial since they have the ability to disrupt any secondary structure of the linker.

In one preferred embodiment is the linker a proline rich linker. In this connection is a proline rich linker intended to mean a linker where at least 20% of the residues are proline residues, preferably between 25 and 50% of the residues.

A preferred example of a proline rich linker according to the invention is -PEPTPEPN- (SEQ ID NO: 1).

In a particularly preferred embodiment, the fusion according to the invention consists of the mature part of SEQ ID NO: 14. It comprises a pulB/C hybrid (fusion) created by expression of a pulB/C gene hybrid (fusion) consisting of the portion of the pulB gene upstream of the BamHI site within the coding region (see Kelly et al., supra) and the portion of the pulC gene of *B. acidopullulyticus* downstream of the BamHI site within the coding region, the SBD derived from the *A. contaminans* α-amylase or the *Thermoanaerobacter* sp. CGTase, and the linker -PEPTPEPN- (SEQ ID NO: 1).

The fusions according to the invention are conveniently produced by providing nucleic acid encoding the fusion of the invention, inserting said nucleic acid into a suitable expression vector having a suitable promoter and suitable regulatory sequences adapted to the particular selected host cell, transforming a host cell with the expression vector, cultivating the transformed host cell in a suitable growth medium promoting the expression of the fusion and subsequently recovering the fusions. Techniques for expressing a recombinant polypeptide such as the fusions according to the invention, expression vectors, host cells etc. are abundantly available in the art and it is within the skills of the average practitioner to select suitable conditions for producing the fusions according to the invention e.g. using well known methods described in Sambrook et al. op. cit.

Recombinant Expression Vectors

In another aspect, the invention relates to a recombinant expression vector comprising nucleic acids encoding a fusion according to the invention.

The recombinant expression vector of the invention may be any expression vector which may conveniently be subjected to recombinant DNA procedures, and the choice of vector often depends on the host cell into which it is going to be introduced. Thus, the vector may be an autonomously replicating vector, i.e. a vector which exists as an extra-chromosomal entity, the replication of which is independent of chromosomal replication, e.g. a plasmid. Alternatively, the vector may be one which, when introduced into a host cell, is integrated into the host cell genome, in part or in its entirety, and replicated together with the chromosome(s) into which it has been integrated. The expression vector may be derived from plasmid or viral DNA, or may contain elements of both.

In an expression vector of this invention, the DNA sequence encoding the fusion preferably is operably linked to additional segments required for transcription of the DNA, in particular one or more promoter and terminator regions. The term, "operably linked", indicates that the segments are arranged so that they function in concert for their intended purposes, e.g. transcription initiates in a promoter and proceeds through the DNA sequence coding for the enzyme.

The promoter may be any DNA sequence which shows transcriptional activity in the host cell of choice and may be derived from genes encoding proteins either homologous or heterologous to the host cell.

Examples of suitable promoters for use in bacterial host cells include the promoter of the *Bacillus stearothermophilus* maltogenic amylase gene, the *Bacillus licheniformis* alpha-amylase gene, the *Bacillus amyloliquefaciens* alpha-amylase gene, the *Bacillus subtilis* alkaline protease gene, or the *Bacillus pumilus* xylosidase gene, or the phage Lambda $P_R$ or $P_L$ promoters or the *E. coli* lac, trp or tac promoters.

The DNA sequence encoding the enzyme of the invention may also, if necessary, be operably connected to a suitable terminator.

The recombinant expression vector of the invention may further comprise a DNA sequence enabling the vector to replicate in the host cell in question.

The expression vector of the invention may also comprise a selectable marker, e.g. a gene the product of which complements a defect in the host cell, or a gene encoding resistance to e.g. antibiotics like kanamycin, chloramphenicol, erythromycin, tetracycline, spectinomycin, or the like, or resistance to heavy metals or herbicides.

To direct the enzyme into the secretory pathway of the host cells, a secretory signal sequence (also known as a leader sequence, prepro sequence or pre sequence) may be provided in the recombinant vector. The secretory signal sequence is joined to the DNA sequence encoding the enzyme in the correct reading frame. Secretory signal sequences are commonly positioned 5' to the DNA sequence encoding the enzyme. The secretory signal sequence may be that normally associated with the enzyme or may be from a gene encoding another secreted protein.

The procedures used to ligate the DNA sequences coding for the present enzyme, the promoter and optionally the terminator and/or secretory signal sequence, respectively, or to assemble these sequences by suitable PCR amplification schemes, and to insert them into suitable vectors containing the information necessary for replication or integration, are well known to persons skilled in the art (cf. e.g. Sambrook et al., op. cit.).

Raw Starch Degradation

In a further aspect the invention relates to a method for degrading raw starch using a polypeptide comprising a catalytic starch debranching domain and a starch binding domain. The inventors have surprisingly realized that a more efficient raw starch degradation can be achieved using a polypeptide comprising a catalytic starch debranching domain and a starch binding domain compared to using a polypeptide comprising same catalytic starch debranching domain but without the starch binding domain.

The polypeptide comprising a catalytic starch debranching domain and a starch binding domain may be a natural enzyme or it may be a fusion according to the invention. Preferably the polypeptide comprising a catalytic starch debranching domain and a starch binding domain is a fusion according to the invention, even more preferred a fusion polypeptide comprising a catalytic pullulanase domain and a starch binding domain.

Typically the method for degrading raw starch comprises the following steps:
a) providing a mixture comprising raw starch and water;
b) adding at least one polypeptide comprising a catalytic starch debranching domain and a starch binding domain, at least one endo acting amylase and at least one exo-acting amylase;
c) incubating the mixture at a suitable temperature and for a sufficient time to obtain the desired degree of degradation.

The mixture in step a) may additionally comprise pH regulating compounds, inorganic salts etc. The raw starch may be any raw starch, but it is preferred that the starch is cereal starch such as starch from corn, wheat, barley, sorghum etc.

The polypeptide comprising a catalytic starch debranching domain and a starch binding domain may be a natural polypeptide or it may be a fusion according to the invention.

The endo acting amylase is preferably an α-amylase selected among α-amylases derived from a microbial source in particular from a filamentous fungus or a yeast, or a bacteria. Numerous α-amylases are known within the art and it is within the capabilities of the skilled person to select a suitable α-amylase for the method for raw starch degradation according to the invention. As examples of suitable α-amylases can be mentioned the α-amylase derived from a strain of *Acremonium*, a strain of *Alcaligenes*, in particular *Alcaligenes latus*, a strain of *Aspergillus*, in particular *Aspergillus kawachii* and *Aspergillus oryzae*, a strain of *Bacillus*, in particular *Bacillus amyloliquefaciens*, *Bacillus licheniformis*, *Bacillus polymyxa*, *Bacillus subtilis* and *Bacillus stearothermophilus*, a strain of *Desulfurococcus*, in particular *Desulfurococcus mucosus*, a strain of *Fervidobacterium*, a strain of *Lactobacillus*, a strain of *Micrococcus*, a strain of *Pseudomonas*, in particular *Pseudomonas amyloderamosa*, a strain of *Pyrococcus*, in particular *Pyrococcus furiosus* and *Pyrococcus woesei*, a strain of *Pyrodictium*, a strain of *Sulfolobus*, a strain of Staphylothermus, or a strain of *Thermococcus* sp.

The exo-acting amylase is preferably a glucoamylase such as a glucoamylase derived from *Aspergillus niger*, *A. awamori*, *A. kawachii*, *Talaromyces emersonii*, *Trametes cingulata* or *Athelia rolfsii*.

The α-amylase and/or the glucoamylase may be (a) natural enzyme(s), or may be (a) variant enzyme(s) modified using well known recombinant DNA technology methods.

In one preferred embodiment is the raw starch degradation a part of process for preparing fuel ethanol.

Other uses contemplated by the inventors include the use of the fusion according to the invention in detergent compositions, starch liquefaction or saccharification or textile desizing.

The invention is not described further by the following examples which are provided for illustrative purposes and not should be considered limiting in any way.

Experimental

Media

*Bacillus* strains were grown on TBAB plates (Difco Tryptose Blood Agar Base (BD Diagnostics, Franklin Lakes, N.J., USA) or LB agar plates (10 g/l Tryptone, 5 g/l yeast extract, 5 g/l NaCl, 15 g/l bacto agar) or in VY liquid medium (25 g/l veal infusion (BD Diagnostics, Franklin Lakes, N.J., USA), 5 g/l yeast extract). As necessary, filter sterilized antibiotics were added to media after autoclaving at the following concentrations: spectinomycin, 120 micro-g/ml; neomycin, 6 micro-g/ml; chloramphenicol, 5 micro-g/ml.

*E. coli* strains were grown on LB liquid medium (10 g/l Tryptone, 5 g/l yeast extract, 5 g/l NaCl) or LB agar (LB medium and 15 g/l bacto agar) or 2×YT agar (16 g/l of Tryptone, 10 g/l of yeast extract, 5 g/l of NaCl, 15 g/l bacto agar) supplemented with 100 micro-g/ml ampicillin (filter sterilized, added after autoclaving).

*Bacillus* Host Strains

*Bacillus subtilis* 168Δ4 is derived from the *Bacillus subtilis* type strain 168 (BGSC 1A1, *Bacillus* Genetic Stock Center, Columbus, Ohio) and has deletions in the spoIIAC, aprE, nprE, and amyE genes. The deletion of these four genes was performed essentially as described for *Bacillus subtilis* A164Δ5, which is described in detail in U.S. Pat. No. 5,891,701.

*B. subtilis* A164Δ10 is strain A164Δ5 with deletions in the minor extracellular protease genes wprA, bpr, vpr, mpr, and epr (Connelly et al., 2004, J. Bacteriol. 186: 4159-4167).

Plasmid and Genomic DNA Isolations

Plasmid DNA was isolated from *E. coli* transformants using a QIAprep 8 Miniprep Kit (QIAGEN, Valencia, Calif., USA) or using a BioRobot 9600 (QIAGEN Inc., Valencia, Calif., USA), or using a QIAGEN Plasmid Midi Kit (QIAGEN Inc., Valencia, Calif., USA) according to the procedure provided by the respective manufacturers.

Genomic DNA was isolated from *Bacillus subtilis* hosts according to the procedure of Pitcher et al., 1989, *Lett. Appl. Microbiol.* 8: 151-156.

Transformation Methods for *E. coli* and *B. subtilis*

*B. subtilis* strains were transformed according to the procedure of Anagnostopolous and Spizizen (*J. Bacteriol.* 81: 741-746).

*E. coli* SURE cells (Stratagene Corporation, La Jolla, Calif., USA), DH5α cells (Gibco BRL, Gaithersburg, Md., USA), and One Shot® TOP10 cells (Invitrogen, Carlsbad, Calif., USA), XL1-Blue cells (Stratagene Corporation, La Jolla, Calif., USA) were transformed according to the procedure provided by the respective manufacturers.

PCR

The PCRs were performed according to the manufacturer's instructions described above. The amplification reactions (50 micro-L) were composed of 1×PCR Buffer II (Applied Biosystems, Foster City, Calif., USA), 3.0 mM $MgCl_2$, 200 micro-M of each dNTP, 0.5 micro-M of each primer, 0.25 units of Taq DNA Polymerase, and approximately 50-100 ng of plasmid DNA or approximately 200 ng of genomic DNA. The reactions were performed in a RoboCycler® 40 Temperature Cycler (Stratagene, La Jolla, Calif., USA) programmed for 1 cycle at 95° C. for 2 minutes; 30 cycles each at 95° C., 55° C., and 72° C. for 2 minutes; and 1 cycle at 72° C. for 3 minutes.

DNA Sequencing

DNA sequencing was performed using an Applied Biosystems Model 3130X Genetic Analyzer (Applied Biosystems, Foster City, Calif., USA) using dye terminator chemistry (Giesecke et al., 1992, *Journal of Virol. Methods* 38: 47-60).

Pullulan-Azure and AZCL-Pullulan Overlays

Pullulanase activity of *Bacillus* strains on agar plates was detected using an agar overlay containing pullulan-azure (Sigma, St. Louis, Mo., USA) or AZCL-pullulan (Megazymes International Ireland Ltd., Bray, Ireland). A layer of 1% agar in 100 mM sodium acetate (pH 5.0) containing 0.5% pullulan-azure or 0.1% AZCL-pullulan was poured over colonies on agar plates, which were then incubated at 50° C. Pullulanase activity was detected by formation of a zone of clearing in the pullulan-azure surrounding a colony.

Enzyme Activities:

Glucoamylase Activity (AGU)

The Novo Glucoamylase Unit (AGU) is defined as the amount of enzyme, which hydrolyzes 1 micromole maltose per minute at 37° C. and pH 4.3.

The activity is determined as AGU/ml by a method modified after (AEL-SM-0131, available on request from Novozymes) using the Glucose GOD-Perid kit from Boehringer Mannheim, 124036. Standard: AMG-standard, batch 7-1195, 195 AGU/ml. 375 micro-L substrate (1% maltose in 50 mM Sodium acetate, pH 4.3) is incubated 5 minutes at 37° C. 25 micro-L enzyme diluted in sodium acetate is added. The reaction is stopped after 10 minutes by adding 100 micro-L 0.25 M NaOH. 20 micro-L is transferred to a 96 well microtiter plate and 200 micro-L GOD-Perid solution (124036, Boehringer Mannheim) is added. After 30 minutes at room temperature, the absorbance is measured at 650 nm and the activity calculated in AGU/ml from the AMG-standard. A folder (AEL-SM-0131) describing this analytical method in more detail is available on request from Novozymes A/S, Denmark, which folder is hereby included by reference.

Pullulanase Activity (New Pullulanase Unit Novo. NPUN)

Pullulanase activity may be determined relative to a pullulan substrate. Pullulan is a linear D-glucose polymer consisting essentially of maltotriosyl units joined by 1,6-alpha-links. Endo-pullulanases hydrolyze the 1,6-alpha-links at random, releasing maltotriose, 63-alpha-maltotriosylmaltotriose, 63-alpha-(63-alpha-maltotriosyl-maltotriosyl)-maltotriose.

One new Pullulanase Unit Novo (NPUN) is a unit of endo-pullulanase activity and is measured relative to a Novozymes A/S Promozyme D standard. Standard conditions are 30 minutes reaction time at 40° C. and pH 4.5; and with 0.7% Red-pullulan as substrate. The amount of red substrate degradation product is measured spectrophotometrically at 510 nm and is proportional to the endo-pullulanase activity in the sample. A folder (EB-SM.0420.02/01) describing this analytical method in more detail is available upon request to Novozymes A/S, Denmark, which folder is hereby included by reference.

Under the standard conditions one NPUN is approximately equal to the amount of enzyme which liberates reducing carbohydrate with a reducing power equivalent to 2.86 micromole glucose per minute.

Media

| SSB-4: Sucrose/Soy/Biotin Agar | |
|---|---|
| Media component | Amount |
| Soy peptone | 10 g/L |
| Sucrose | 10 g/L |
| $Na_3$-citrate-$2H_2O$ | 2 g/L |
| $KH_2PO_4$ | 4 g/L |
| $Na_2HPO_4$ | 5 g/L |
| 0.15 mg/mL Biotin | 1 mL/L |
| Ms-2 (Mikrosoy) | 6 mL/L |
| Bacto Agar | 15 g/L |

| PRK50 shake flask media | |
|---|---|
| Media component | Amount |
| Soybean meal | 110 g/L |
| $Na_2HPO_4$ | 5 g/L |
| SB2121 (antifoam) | 1 mL/L |

Adjust to pH 7 with NaOH

| DK Pullulanase media | |
|---|---|
| Media component | Amount |
| J6 Hydrolysate | 490 g/L |
| $K_2SO_4$ | 6 g/L |
| $Na_2HPO_4$ | 5 g/L |
| $K_2HPO_4$ | 12 g/L |
| SB2121 | 1.25 mL/L |
| $(NH_4)_2SO_4$ | 4 g/L |
| $CaCO_3$ | 0.34 g/L |
| Citric acid | 2 g/L |
| $MgSO_4 \cdot 7H_2O$ | 4 g/L |
| Sporemetal premix (from DK pilot) | 40 mL/L |
| 0.3 mg/mL biotin stock solution | 2 mL/L |

| Sucrose Feed | |
|---|---|
| Media component | Amount |
| Sucrose | 708 g/L |
| SB2121 | 4 mL/L |

J6: Tubermine Potato Protein Hydrolysate

To make 10 L, add 5 L tap water and 0.75 kg Tubermine to 12 L fermentor

Add water to 8 L, agitate for full suspension (500 rpm)

Start heating to 55° C.

At 55° C., add 4N NaOH to pH 7.00

At pH=6.20 viscosity will increase

At pH=7.00, add 72.9 g Alcalase 2.4

4 HR hydrolysis

Fill with water to 9 L

At 5 HRs total, reduce agitation to 300 rpm

Stop titration

Add water to 10 L

EXAMPLES

Example 1

Construction of pNBT36 pNBT36 is pDG268MCSΔ-P$_{amyQ(sc)}$/P$_{cryIIIA}$/cryIIIAstab/SAV with fragments of the *Bacillus subtilis* amy E gene, permitting insertion of the expression cassette at the amy E locus of the *Bacillus subtilis* chromosome by double homologous recombination via the two amy E fragments using chloramphenicol selection. The construction of pNBT36 is described below.

Figure 2:
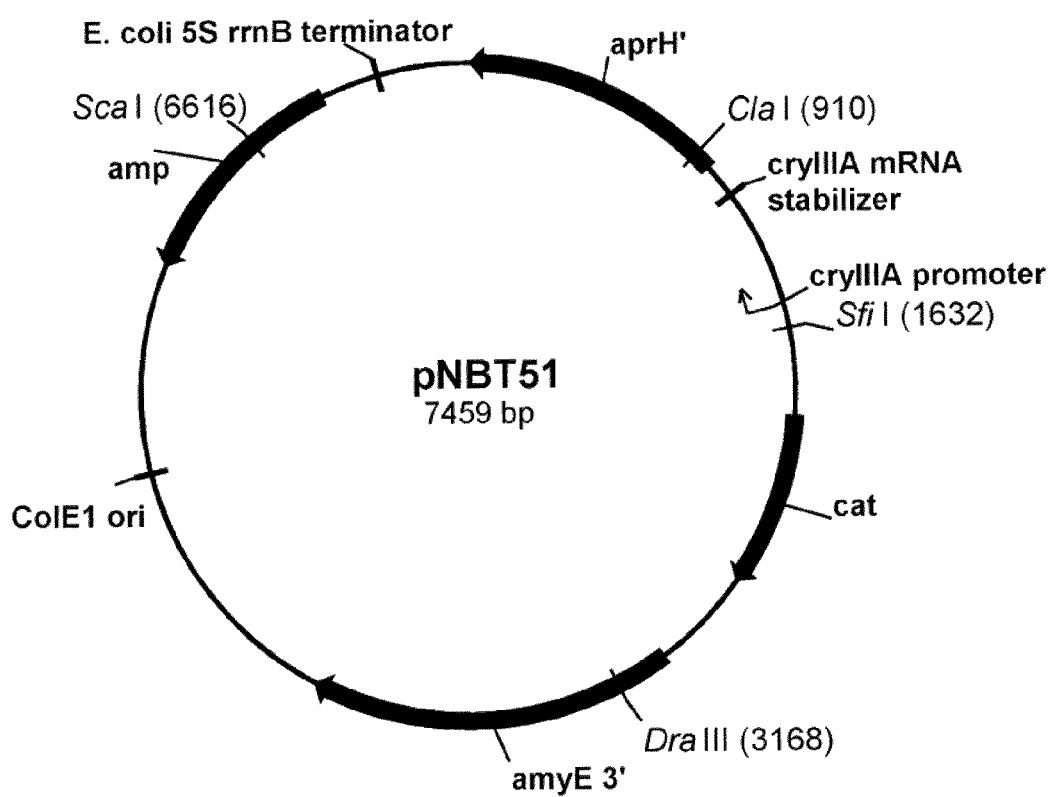

Plasmid pNBT51. Plasmid pNBT10 (pDG268MCS-Pr$_{cryIIIA}$/cryIIIAstab/SAV; U.S. Pat. No. 6,255,076) was isolated from *E. coli* host DH5α according to the manufacturer's instructions, and digested with Cla I and Sca I. The Cla I ends were blunted using Klenow fragment (New England Biolabs, Inc., Beverly, Mass., USA) and dNTPs according to the manufacturer's instructions. The digested plasmid was analyzed by 0.8% agarose electrophoresis with TBE (50 mM Tris base-50 mM boric acid-1 mM disodium EDTA) buffer, and a vector fragment of approximately 6615 bp was purified using a QIAquick Gel Extraction Kit (QIAGEN Inc., Valencia, Calif., USA). Plasmid pOS4301 (Bacillus Genetic Stock Center, Ohio State University, Columbus, Ohio, USA) was digested with Sal I and Sca I, and the Sal I ends were blunted using Klenow fragment and dNTPs, as described above. The digested plasmid was analyzed by 0.8% agarose electrophoresis with TBE buffer, and a fragment of approximately 840 bp bearing the *E. coli* rrnB transcription terminator was purified using a QIAquick Gel Extraction Kit. The same 840 bp Sal I/Sca I fragment could be isolated from the vector pKK223-3 (GE Healthcare, Piscataway, N.J., USA) (FIG. 1). The pNBT10 vector fragment and terminator-bearing fragment were ligated together with T4 DNA ligase (Roche Diagnostics Corporation, Indianapolis, Ind., USA) according to the manufacturer's instructions, and *E coli* DH5α was transformed with the ligation according to the manufacturer's instructions, selecting for ampicillin resistance on 2×YT ampicillin plates at 37° C. The resulting plasmid was designated pNBT51 (pDG268-P$_{cryIIIA}$/cryIIIAstab/SAVΔ) (FIG. 2).

Figure 3:
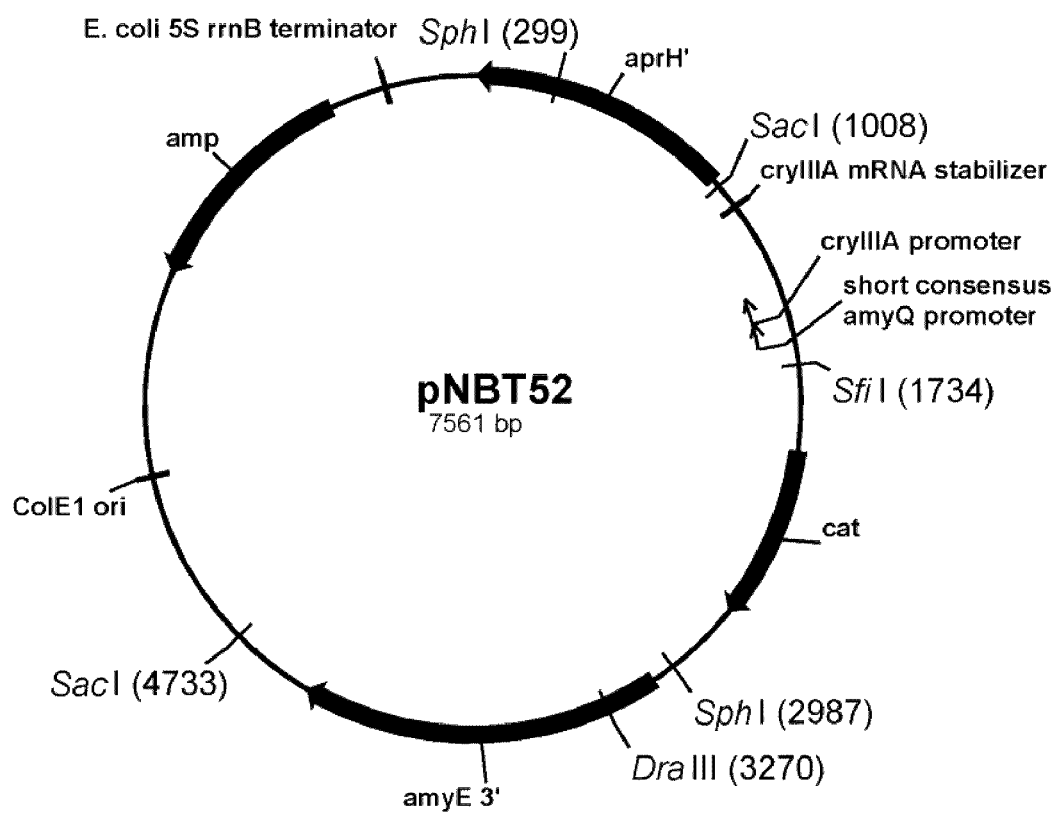

Plasmid pNBT52. Plasmid pNBT51 (pDG268-P$_{cryIIIA}$/cryIIIAstab/SAVΔ) was digested with Sfi I, and the ends were blunted by incubation for 20 minutes at 11° C. with T4 DNA polymerase (Roche Diagnostics Corporation, Indianapolis, Ind., USA) and 25 micro-M of each dNTP, followed by heat-inactivation of the polymerase by incubation for 10 minutes at 75° C. The blunt-ended plasmid was then digested with Dra III and analyzed by 0.8% agarose electrophoresis with TBE buffer, and a vector fragment of approximately 5920 bp was purified using a QIAquick Gel Extraction Kit. Plasmid pNBT20 (pDG268MCS-P$_{amyQ(sc)}$/SAV; U.S. Pat. No. 6,255,076) was digested with Dra III and Ecl 136II, and a fragment of approximately 1641 bp bearing a short consensus amyQ promoter (P$_{amyQ(sc)}$) was purified using a QIAquick Gel Extraction Kit. The pNBT51 vector fragment and P$_{amyQ(sc)}$ fragment were ligated as described above, and *E. coli* DH5α was transformed with the ligation as described above, selecting for ampicillin resistance on 2×YT ampicillin plates at 37° C. Plasmid DNA was isolated from several transformants, digested with Sph I, and analyzed by 0.8% agarose electrophoresis with TBE buffer. One plasmid with expected restriction fragments of approximately 4873 bp and 2688 bp was designated pNBT52 (pDG268-P$_{amyQ(sc)}$/P$_{cryIIIA}$/cryIIIAstab/SAVΔ) (FIG. 3).

Figure 4:
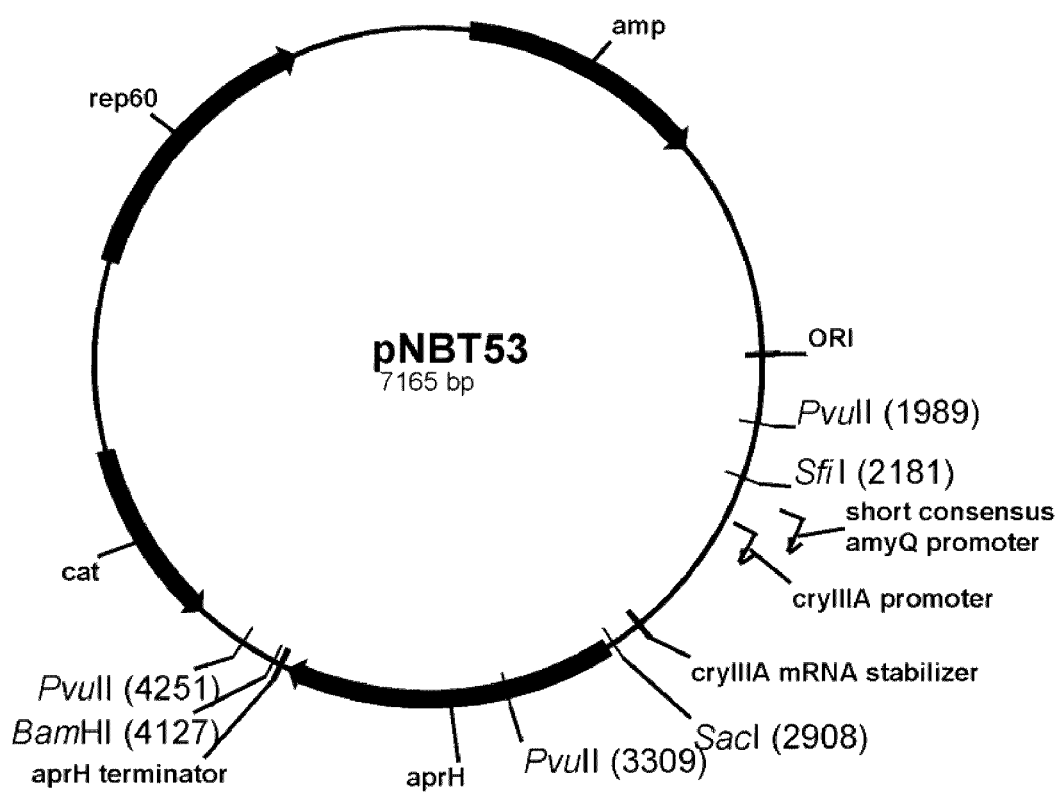

Plasmid pNBT53. Plasmid pNBT6 (pHP13amp-SAV; U.S. Pat. No. 6,255,076) was digested with Sfi I and Sac I and analyzed by 0.8% agarose electrophoresis with TBE buffer, and a vector fragment of approximately 6438 bp was purified using a QIAquick Gel Extraction Kit. Plasmid pNBT52 (pDG268-P$_{amyQ(sc)}$/P$_{cryIIIA}$/cryIIIAstab/SAVΔ) was digested with Sfi I and Sac I and analyzed by 0.8% agarose electrophoresis with TBE buffer, and a fragment of approximately 727 bp bearing the P$_{amyQ(sc)}$/P$_{cryIIIA}$/cryIIIAstab tandem promoter was purified using a QIAquick Gel Extraction Kit. The pNBT6 vector fragment and P$_{amyQ(sc)}$/P$_{cryIIIA}$/cryIIIAstab fragment were ligated as described above, and *E coli* DH5α cells were transformed with the ligation as described above, selecting for ampicillin resistance on 2×YT ampicillin plates at 37° C. Plasmid DNA was isolated from several transformants, digested with Pvu II, and analyzed by 0.8% agarose electrophoresis using TBE buffer. One plasmid with expected restriction fragments of approximately 4903 bp, 1320 bp, and 942 bp was designated pNBT53 (pHP13amp-P$_{amyQ(sc)}$/P$_{cryIIIA}$/cryIIIAstab/SAV) (FIG. 4).

Figure 5:
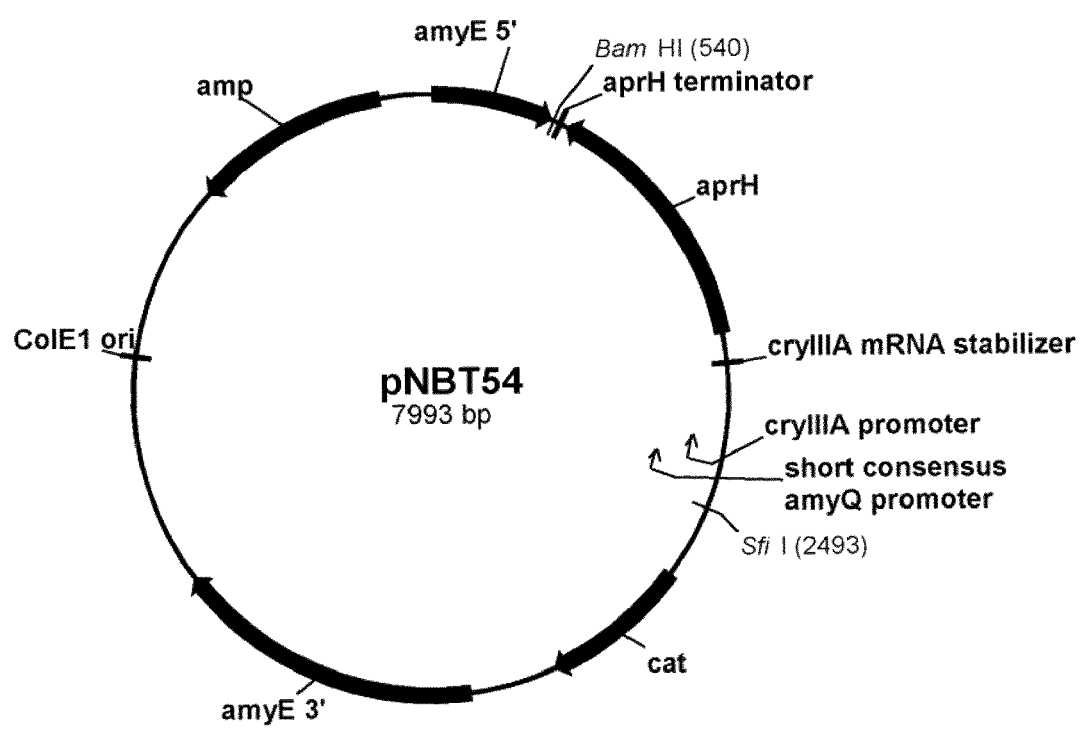

Plasmid pNBT54. Plasmid pNBT1 (pDG268MCS; U.S. Pat. No. 6,255,076) was digested with Sfi I and Bam HI and analyzed by 0.8% agarose electrophoresis with TBE buffer, and a vector fragment of approximately 6040 bp was purified using a QIAquick Gel Extraction Kit. Plasmid pNBT53 (pHP13amp-P$_{amyQ(sc)}$/P$_{cryIIIA}$/cryIIIAstab/SAV) was digested with Sfi I and Bam HI and analyzed by 0.8% agarose electrophoresis using TBE buffer, and a fragment of approximately 1953 bp bearing the P$_{amyQ(sc)}$/P$_{cryIIIA}$/cryIIIAstab/SAV cassette was purified using a QIAquick Gel Extraction Kit. The pNBT1 vector fragment and P$_{amyQ(sc)}$/P$_{cryIIIA}$/cryIIIAstab/SAV fragment were ligated as described above, and *E. coli* DH5α cells were transformed with the ligation as described above, selecting for ampicillin resistance on 2×YT ampicillin plates at 37° C. Plasmid DNA was isolated from several transformants and analyzed by simultaneous digestion with Sfi I and Bam HI followed by 0.8% agarose gel electrophoresis with TBE buffer. One plasmid with expected restriction fragments of approximately 6040 bp and 1953 bp was designated pNBT54 (pDG268MCS-P$_{amyQ(sc)}$/P$_{cryIIIA}$/cryIIIAstab/SAV) (FIG. 5).

Figure 6:
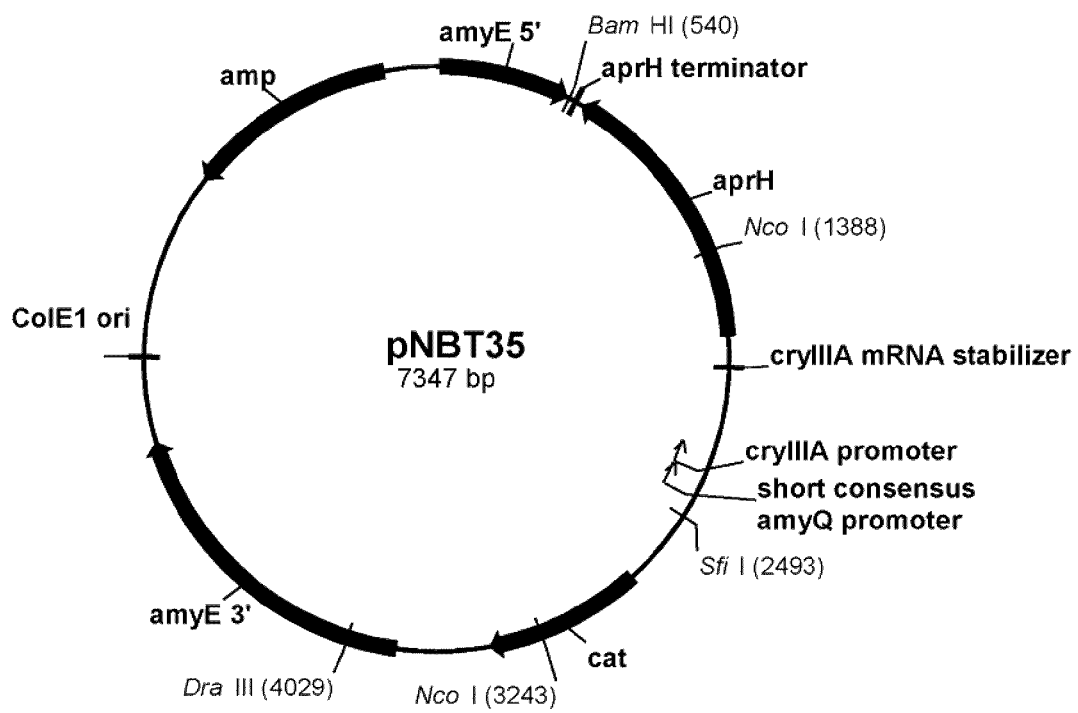

Plasmid pNBT35. Plasmid pNBT2 (pDG268MCSΔ-Pr$_{cryIIIA}$/cryIIIAstab/SAV; U.S. Pat. No. 6,255,076) was digested with Sfi I and Bam HI and analyzed by 0.8% agarose gel electrophoresis with TBE buffer, and a vector fragment of approximately 5394 bp was purified using a QIAquick Gel Extraction Kit. Plasmid pNBT54 (pDG268MCS-P$_{amyQ(sc)}$/P$_{cryIIIA}$/cryIIIAstab/SAV) was digested with Sfi I and Bam HI, and analyzed by 0.8% agarose gel electrophoresis with TBE buffer, and a fragment of approximately 1953 bp bearing the P$_{amyQ(sc)}$/P$_{cryIIIA}$/cryIIIAstab/SAV cassette was purified using a QIAquick Gel Extraction Kit. The pNBT2 vector fragment and P$_{amyQ(sc)}$/P$_{cryIIIA}$/cryIIIAstab/SAV fragment were ligated as described above, and *E. coli* DH5α cells were transformed with the ligation as described above, selecting for ampicillin resistance on 2×YT ampicillin plates at 37° C. Plasmid DNA was isolated from several transformants, digested with Nco I, and analyzed by 0.8% agarose gel electrophoresis with TBE buffer. One plasmid with expected restriction fragments of approximately 5492 bp and 1855 bp was designated pNBT35 (pDG268MCSΔ-P$_{amyQ(sc)}$/P$_{cryIIIA}$/cryIIIAstab/SAV) (FIG. 6).

Plasmid pNBT30. Plasmid pNBT30 was constructed to contain a PCR clone of the amyL4199 variant of the amyL gene promoter (U.S. Pat. No. 6,100,063). *Bacillus licheniformis* SJ1904 genomic DNA was isolated. The amyL4199 promoter (P$_{amyL4199}$) gene was amplified by PCR from *Bacillus*

*licheniformis* SJ1904 genomic DNA using primers 950872 and 991151 (SEQ ID NO: 2 and 3). Primer 950872 incorporates an Sfi I restriction site, and primer 991151 incorporates a Sac I restriction site and the variant nucleotides of $P_{amyL4199}$.

Figure 7:
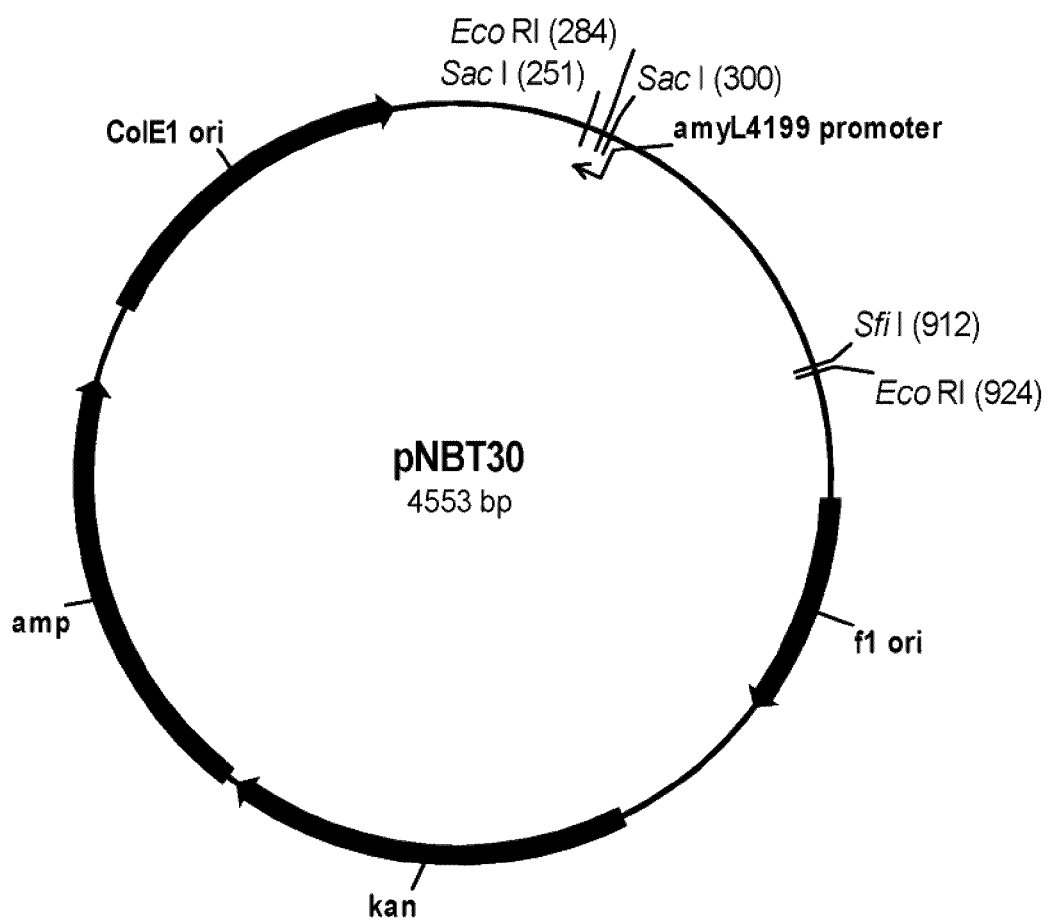

The PCR was performed according to manufacturer's recommendations described above. The resulting PCR product of approximately 625 bp was cloned into vector pCR2.1 using a TOPO TA Cloning® Kit (Invitrogen, Carlsbad, Calif., USA) and transformed into One Shot® TOP10 Chemically Competent *E. coli* cells according to the manufacturer's instructions. Plasmid DNA was isolated from several transformants and analyzed for the presence of the cloned PCR fragment by digestion with Eco RI followed by 0.8% agarose electrophoresis with TBE buffer. One plasmid with expected restriction fragments of approximately 3913 bp and 640 bp was designated pNBT30 (pCR2.1-amyL4199) (FIG. 7). The DNA sequence of the cloned PCR fragment was confirmed by DNA sequencing.

Figure 8:
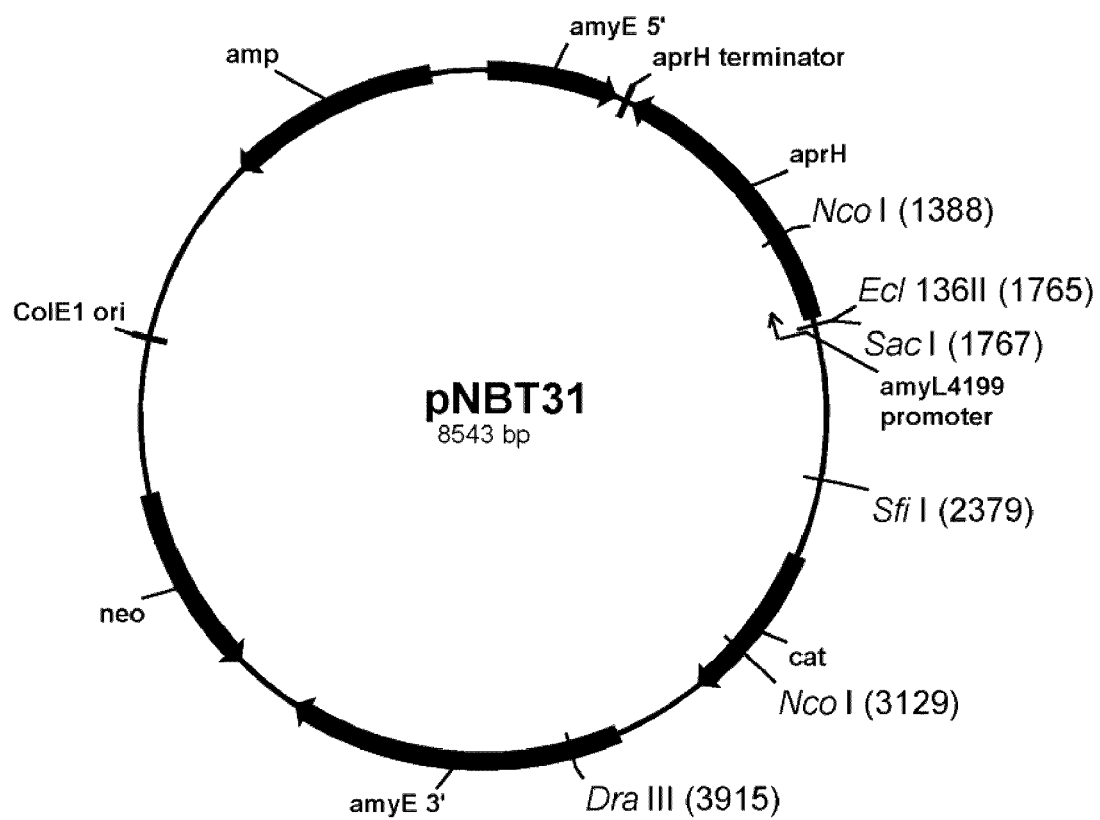

Plasmid pNBT31. Plasmid pNBT3 (pDG268MCSΔneo-Pr$_{cryIIIA}$/cryIIIAstab/SAV; U.S. Pat. No. 6,255,076) was digested with Sfi I and Sac I and analyzed by 0.8% agarose electrophoresis with TBE buffer, and a vector fragment of approximately 7931 bp was purified using a QIAquick Gel Extraction Kit. Plasmid pNBT30 (pCR2.1-amyL4199) was digested with Sfi I and Sac I, analyzed by 0.8% agarose electrophoresis with TBE buffer, and a fragment of approximately 612 bp bearing $P_{amyL4199}$ was purified using a QIAquick Gel Extraction Kit. The pNBT3 vector fragment and $P_{amyL4199}$ fragment were ligated as described above, and *E. coli* XL1-Blue cells were transformed with the ligation according to the manufacturer's instructions, selecting for ampicillin resistance on 2×YT ampicillin plates at 37° C. Plasmid DNA was isolated from several transformants, digested with Nco I, and analyzed by 0.8% agarose electrophoresis with TBE buffer. One plasmid with expected restriction fragments of approximately 6802 bp and 1741 bp was designated pNBT31 (pDG268MCSΔneo-P$_{amyL4199}$/Pr$_{cryIIIA}$/cryIIIAstab/SAV) (FIG. 8).

Figure 9:
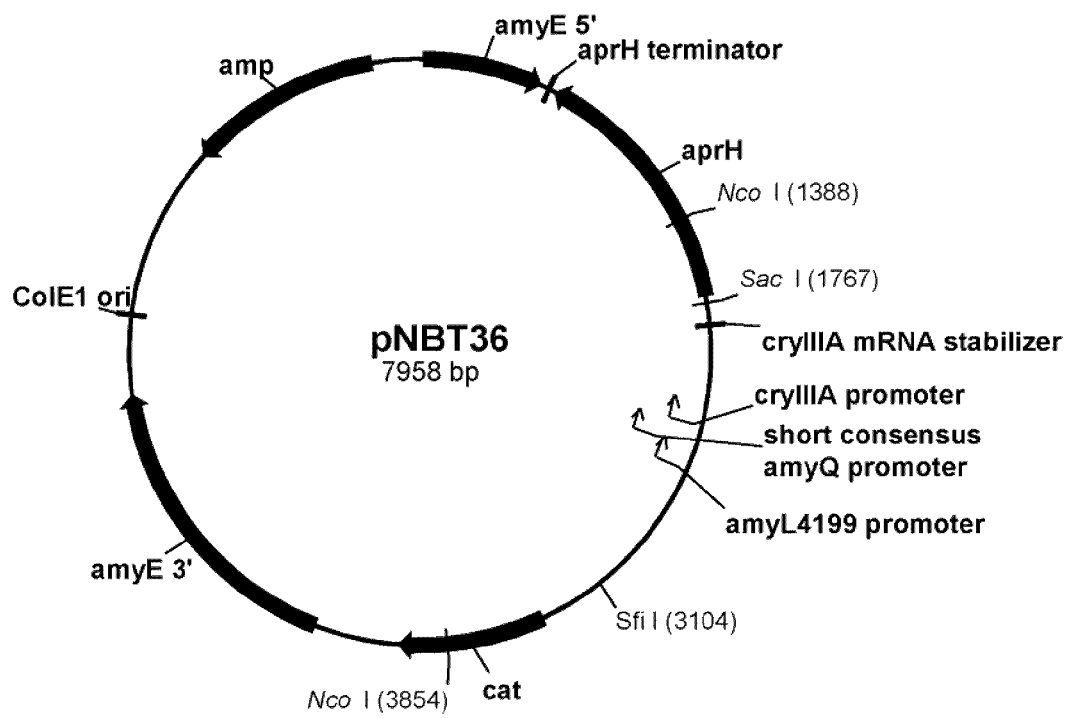

Plasmid pNBT36. Plasmid pNBT35 (pDG268MCSΔ-P$_{amyQ(sc)}$/P$_{cryIIIA}$/cryIIIAstab/SAV) was digested with Sfi I, and the ends were blunted using T4 DNA polymerase and dNTPs, as described above. The blunt ended plasmid was then digested with Dra III, and analyzed by 0.8% agarose electrophoresis with TBE buffer. A vector fragment of approximately 5808 bp was purified using a QIAquick Gel Extraction Kit. Plasmid pNBT31 (pDG268MCSΔneo-P$_{amyL4199}$/Pr$_{cryIIIA}$/cryIIIAstab/SAV) was digested with Dra III and Ecl 136II, analyzed by 0.8% agarose electrophoresis with TBE buffer, and a fragment of approximately 2150 bp bearing $P_{amyL4199}$ was purified using a QIAquick Gel Extraction Kit. The pNBT35 vector fragment and $P_{amyL4199}$ fragment were ligated as described above, and *E. coli* SURE cells were transformed with the ligation according to the manufacturer's instructions, selecting for ampicillin resistance on 2×YT ampicillin plates at 37° C. Plasmid DNA was isolated from several transformants, digested with Nco I, and analyzed by 0.8% agarose electrophoresis with TBE buffer. One plasmid with expected restriction fragments of approximately 5492 bp and 2466 bp was designated pNBT36 (pDG268MCSΔ-P$_{amyL4199}$/P$_{amyQ(sc)}$/P$_{cryIIIA}$/cryIIIAstab/SAV) (FIG. 9). The promoter P$_{amyL4199}$/P$_{amyQ(sc)}$/P$_{cryIIIA}$/cryIIIAstab will henceforth be referred to as triple tandem promoter.

Example 2

Construction of pRB165

Plasmid pRB165 is plasmid pRB162 (pDG268MCS-P$_{amyQ(sc)}$ with fragments of the *Bacillus subtilis* pectate lyase (per) gene, permitting insertion of the expression cassette at the pel locus of the *Bacillus subtilis* chromosome by double homologous recombination via the two pel fragments. U.S. Patent Application publication No. 20030175902) constructed to contain a PCR clone of the spectinomycin resistance gene as described below.

Plasmid pCR2.1-spc. The spectinomycin resistance gene was amplified by PCR from plasmid pSJ5218 (U.S. Pat. No. 6,808,896) DNA using primers 994079 and 994103 (SEQ ID NO: 4 and 5). Primer 994079 incorporates a Sal I restriction site, and primer 994103 incorporates a Sfi I restriction site.

The PCR was performed according to manufacturer's recommendations described above. The PCR was performed in a RoboCycler® 40 Temperature Cycler as described above.

The resulting PCR product of approximately 1165 bp was cloned into vector pCR2.1 using a TOPO TA Cloning® Kit and transformed into One Shot® TOP10 Chemically Competent *E. coli* cells according to the manufacturer's instructions. Plasmid DNA was isolated from several transformants and analyzed for the presence of the cloned PCR fragment by digestion with Eco RI followed by 0.8% agarose electrophoresis with TBE buffer. One plasmid with expected restriction fragments of approximately 3913 bp and 1183 bp was designated pCR2.1-spc. The DNA sequence of the spectinomycin gene was confirmed by DNA sequencing.

Figure 10:
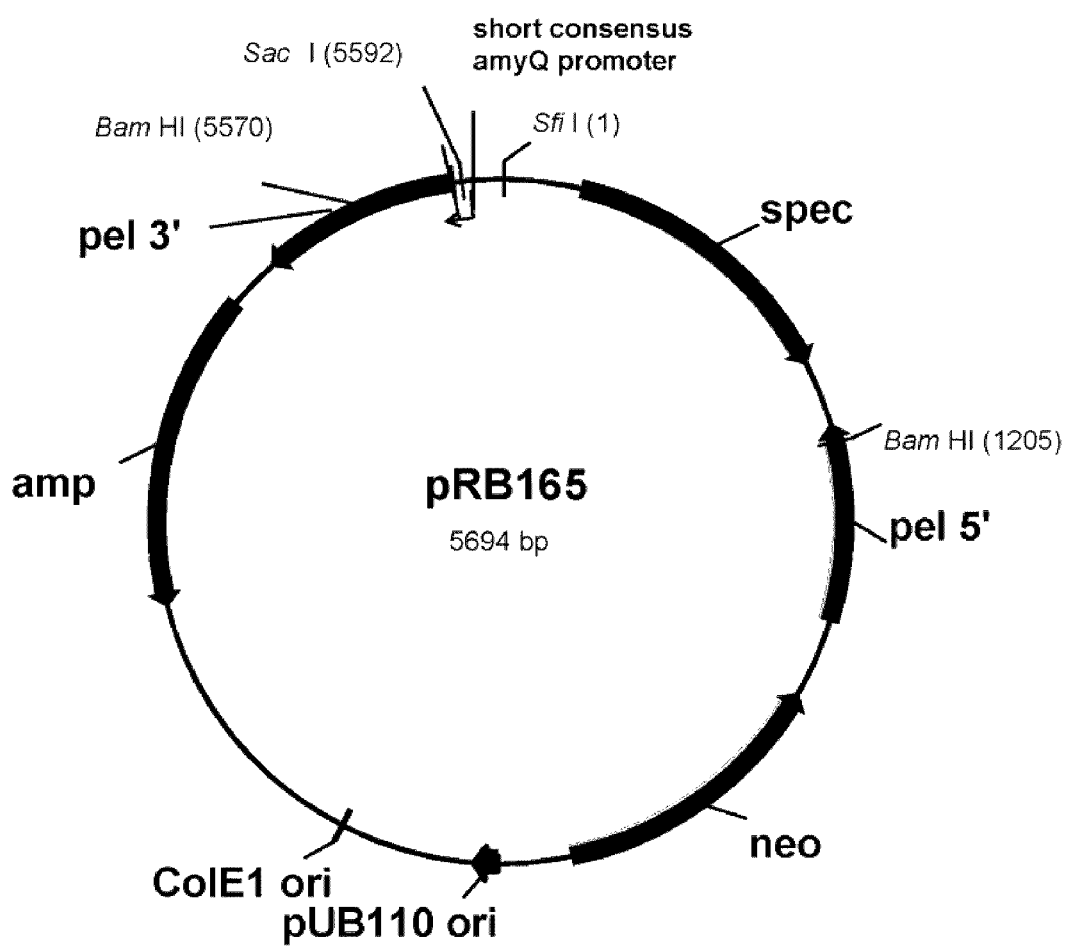

Plasmid pRB165. Plasmid pRB162 (pDG268MCS-P$_{amyQ(sc)}$ with pel 3' and pel 5') was digested with Sfi I and Sal I analyzed by 0.8% agarose electrophoresis with TBE buffer, and a vector fragment of approximately 4541 bp was purified using a QIAquick Gel Extraction Kit. Plasmid pCR2.1/spc was digested with Sfi I and Sal I, and a fragment of approximately 1153 bp bearing the spc gene was purified using a QIAquick Gel Extraction Kit. The pRB162 vector fragment and the spc gene fragment were ligated as described above, and *E. coli* SURE cells were transformed with the ligation as described above, selecting for ampicillin resistance on 2×YT ampicillin plates at 37° C. Plasmid DNA was isolated from several transformants, digested with Bam HI and analyzed by 0.8% agarose electrophoresis with TBE buffer. One plasmid with expected restriction fragments of approximately 1329 bp and 4365 bp was designated pRB165 (pDG268MCS-P$_{amyQ(sc)}$ with pel 3', pel 5', and spc) (FIG. 10).

Example 3

Construction of pMRT135

Figure 11:
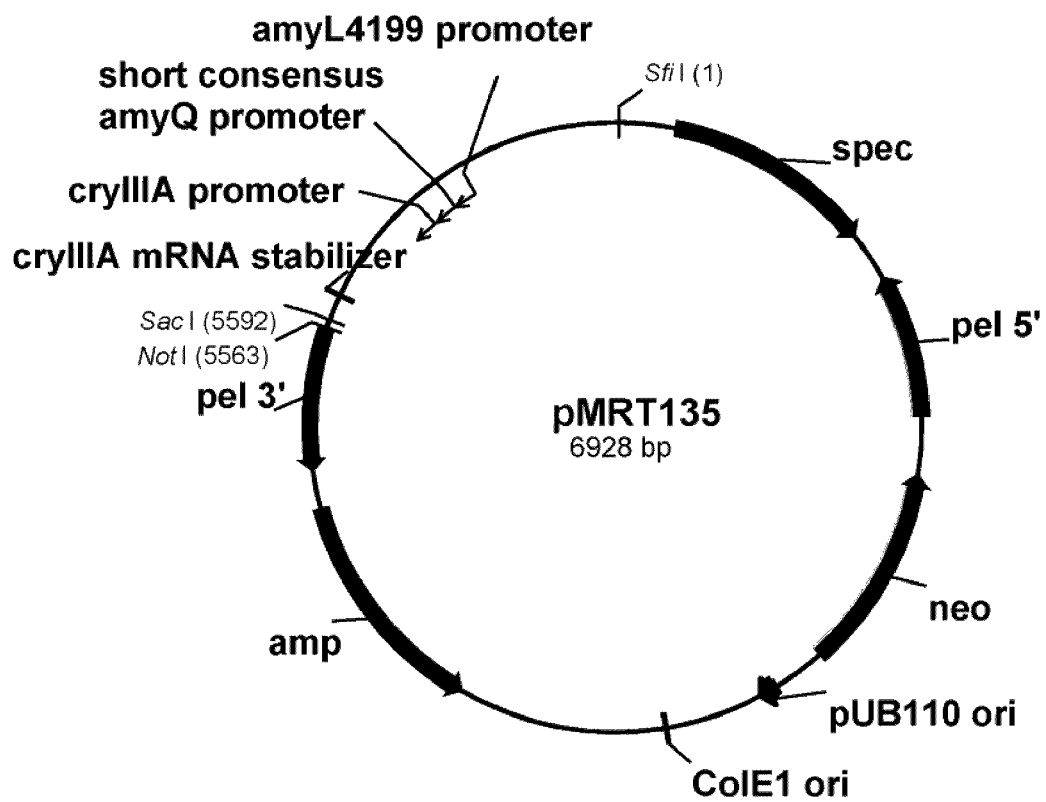

Plasmid pMRT135. Plasmid pNBT36 (pDG268Δ-PamyL4199/PamyQ(sc)/PcryIIIA/cryIIIAstab/SAV) was digested with Sfi I and Sac I and a fragment of approximately 1337 bp bearing the triple tandem promoter was purified using a QIAquick Gel Extraction Kit. Plasmid pRB165 (pDG268Δneo-PamyQ(sc) with pel 3', pel 5', and spc) was digested with Sfi I and Sac I, analyzed by 0.8% agarose electrophoresis with TBE buffer, and a vector fragment of approximately 5591 bp was purified using a QIAquick Gel Extraction Kit. The pRB165 vector fragment and triple tandem promoter fragment were ligated as described above, and *E. coli* SURE cells were transformed with the ligation as described above, selecting for ampicillin resistance on 2×YT ampicillin plates at 37° C. Plasmid DNA was isolated from several transformants, digested with Sfi I and Sac I and analyzed by 0.8% agarose electrophoresis with TBE buffer. One plasmid with expected restriction fragments of approximately 5591 bp and 1337 bp was designated pMRT135 (pDG268Δneo-triple tandem promoter with pel 3', pel 5', and spc) (FIG. 11).

Example 4

Construction of pMDT105

Plasmid pMDT114. Plasmid pMDT114 (FIG. 14) consists of the approximately 5358 bp Sac I/Not I vector fragment of pMRT075 (US Patent Application publication No. 20050221446), the approximately 2622 bp Sac I/Mlu I fragment of pMDT105 (bearing the aprH ribosome binding site and pulB/C coding region), and the approximately 70 bp MluI/NotI fragment of pWWi006 (bearing the aprH transcription terminator). The construction of the plasmids pMDT105 and pWWi006 is described below.

Figure 12:
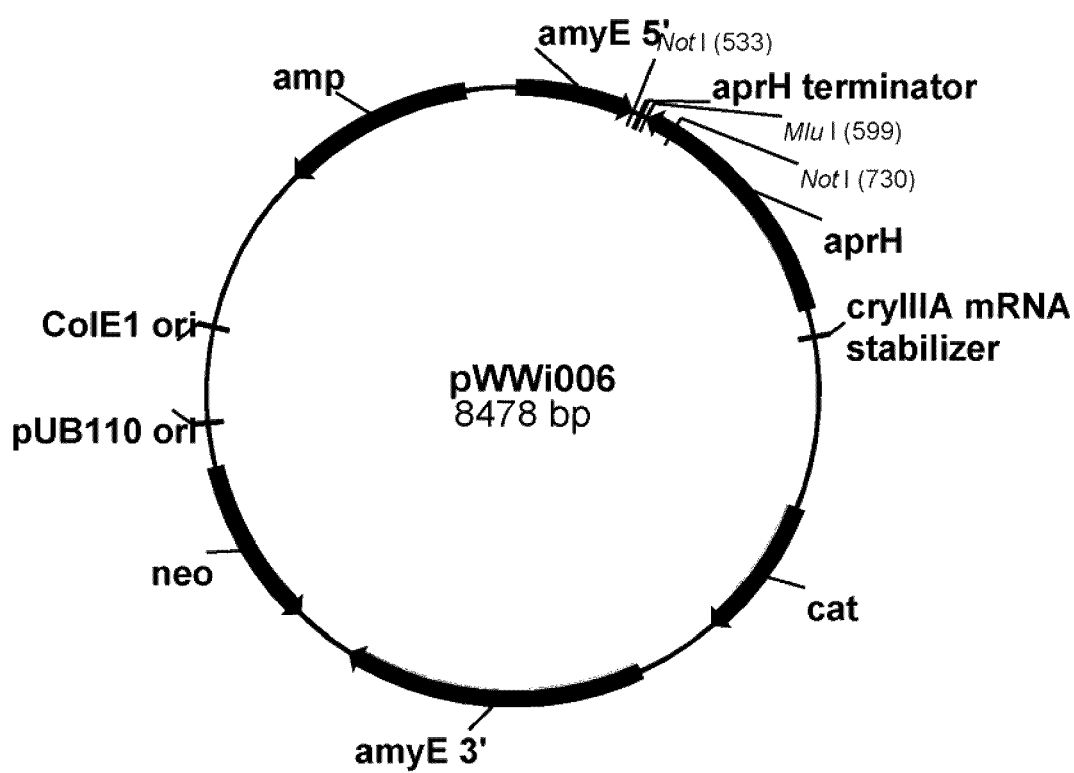

Plasmid pWWi006. pWWi006 was constructed by eliminating the Bam HI site of pNBT18 (pDG268MCSΔneo-cryII-IAstab/SAV; U.S. Pat. No. 5,955,310). Plasmid pNBT18 was digested with Bam HI, and the ends were blunted using T4 DNA polymerase according to the manufacturer's instructions. The pNBT18 vector fragment was then self-ligated using T4 DNA ligase according to the manufacturer's instructions, and E coli DH5α was transformed with the ligation according to the manufacturers instructions, selecting for ampicillin resistance on 2×YT ampicillin plates at 37° C. The resulting plasmid was designated pWWi006 (FIG. 12).

Plasmid pMDT105. Plasmid pMDT105 comprises the aprH ribosome binding site and pulB/C coding region inserted in the pCR2.1 vector and was constructed as follows.

Bacillus subtilis PL2545 contains a chromosomally integrated copy of the pulB/C gene hybrid (fusion). The pulB/C gene comprises a portion of the pulB gene of Bacillus acidopullulyticus 294-16 (Kelly et al., supra) upstream of the BamHI site within the coding region and a portion of the pulC gene of Bacillus acidopullulyticus 246-49 downstream of the BamHI site within the coding region.

An approximately 2624 bp fragment comprising the pulB/C ribosome binding site and coding region was amplified by PCR from genomic DNA of Bacillus subtilis PL2545 using primers 998542 and 998543 (SEQ ID NO: 6 and 7). Primer 998542 incorporates a Sac I restriction site and the ribosome binding site of Bacillus clausii alkaline protease gene aprH and converts the native GTG start codon of pulB to an ATG codon. Primer 998543 incorporates an Mlu I restriction site.

The resulting PCR product of approximately 2624 bp was cloned into pCR2.1 using a TOPO TA Cloning® Kit and transformed into One Shot® TOP10 Chemically Competent E. coli cells according to the manufacturer's instructions. Plasmid DNA from several transformants was purified and the DNA sequence of the cloned PCR fragment was determined by DNA sequencing. Each sequenced plasmid had at least one sequence discrepancy relative to the expected sequence for pulB/C, due to incorporation errors by Taq DNA polymerase. A plasmid with one nucleotide discrepancy within pulB/C was designated pMDT103. This discrepancy was correct as follows, using a fragment of the pulB gene.

An approximately 2624 bp fragment comprising the pulB ribosome binding site and coding region was amplified by PCR from genomic DNA of Bacillus subtilis DN1400 (Kelly et al., supra) using primers 998542 and 998543 shown above.

The PCR was performed according to the manufacturer's instructions as described above.

The resulting PCR product of approximately 2624 bp was cloned into pCR2.1 using a TOPO TA Cloning® Kit and transformed into One Shot® TOP10 Chemically Competent E. coli cells according to the manufacturer's instructions. Plasmid DNA from several transformants was purified and tested for the presence of the cloned PCR fragment by digestion with Eco RI followed by 0.8% agarose electrophoresis with TBE buffer. One plasmid with Eco RI fragments of approximately 3913 bp and 2642 bp was designated pMDT102.

Figure 13:
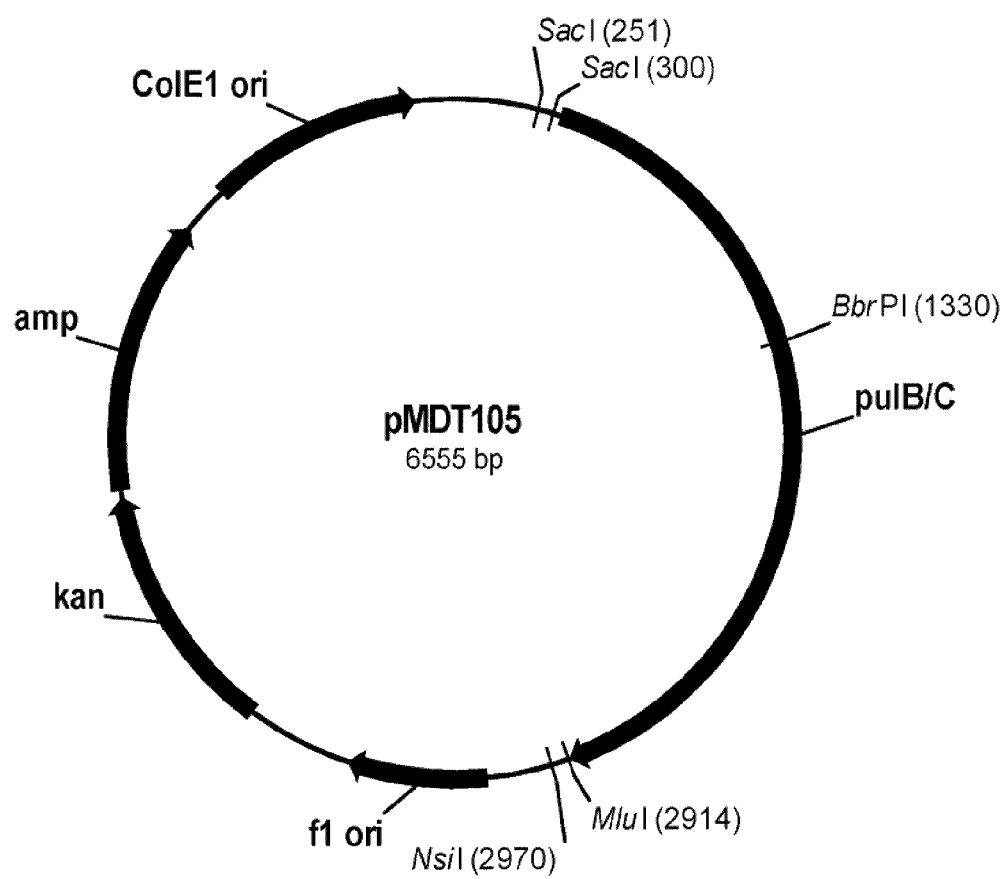
Figure 14:
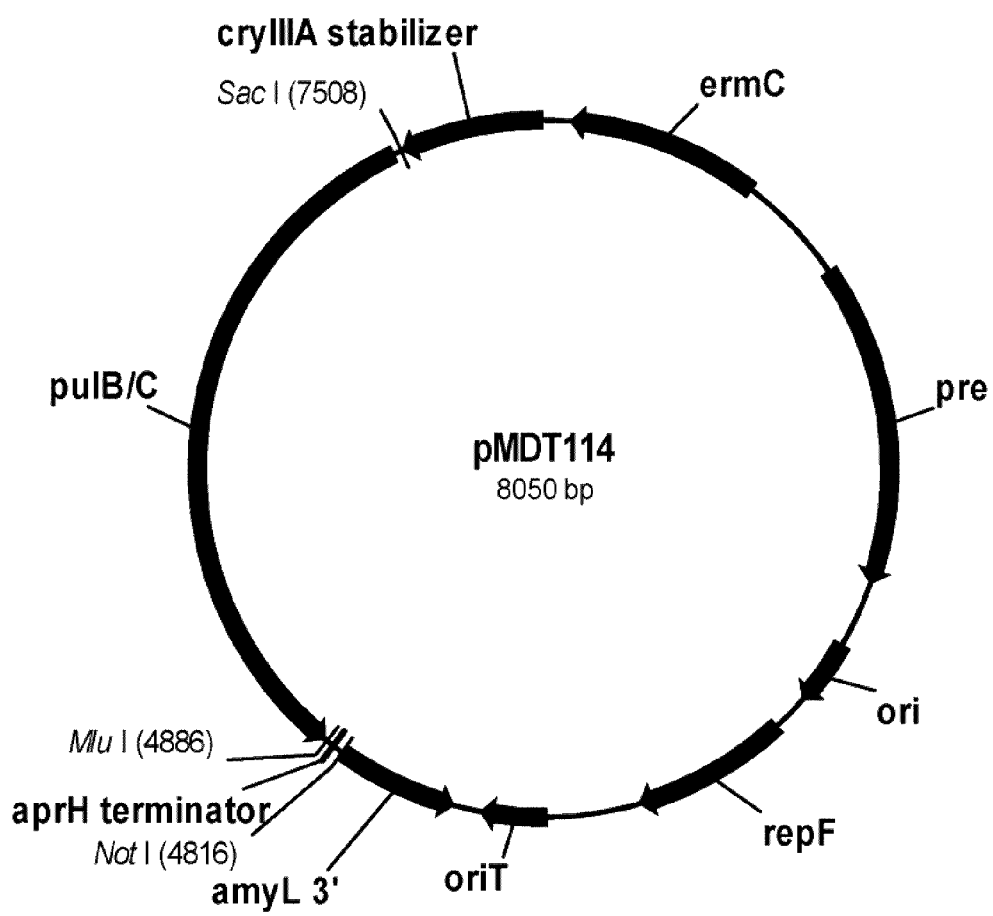

Plasmid pMDT102 was digested with Bbr PI and Nsi I and analyzed by 0.8% agarose electrophoresis with TBE buffer, and a vector fragment of approximately 4915 bp was purified using a QIAquick Gel Extraction Kit (QIAGEN Inc., Valencia, Calif., USA). Plasmid pMDT103 was digested with Bbr PI and Nsi I and analyzed by 0.8% agarose electrophoresis with TBE buffer, and a fragment of approximately 1640 bp bearing a downstream portion of the pulB/C coding region was purified using a QIAquick Gel Extraction Kit. The pMDT102 vector fragment and pulB/C fragment were ligated as described above, and E. coli XL1-Blue cells were transformed with the ligation as described above, selecting for ampicillin resistance on 2×YT ampicillin plates at 37° C. Plasmid DNA was isolated from several transformants, digested with BbrPI and NsiI, and analyzed by 0.8% agarose electrophoresis with TBE buffer. One plasmid with expected restriction fragments of approximately 4915 bp and 1640 bp was designated pMDT105 (FIG. 13).

Example 5

Construction of pMBin115

Figure 15:
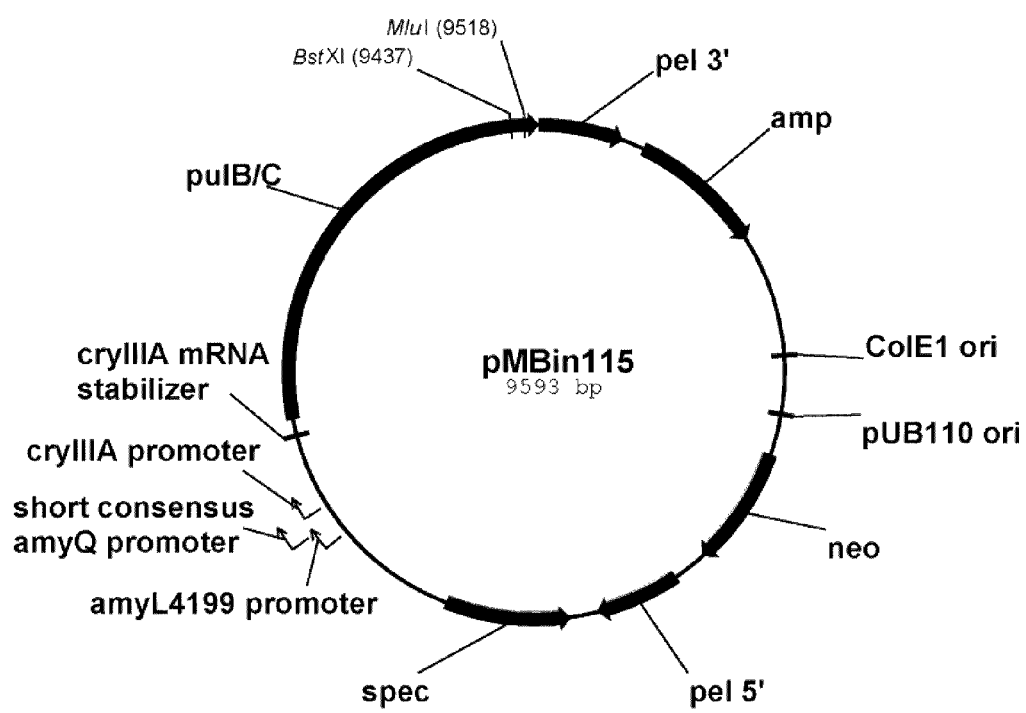

Plasmid pMBin115. Plasmid pMDT114 was digested with Sac I and Not I, analyzed by 0.8% agarose electrophoresis with TBE buffer and a fragment of approximately 2684 bp bearing the pulB/C gene was purified using a QIAquick Gel Extraction Kit. Plasmid pMRT135 (pDG268Δneo-triple tandem promoter with pet 3', pet 5', and spc) was digested with Sac I and Not I, analyzed by 0.8% agarose electrophoresis with TBE buffer, and a vector fragment of approximately 6909 bp was purified using a QIAquick Gel Extraction Kit. The pMRT135 vector fragment and pulB/C fragment were ligated as described above, and E coli SURE cells were transformed with the ligation as described above, selecting for ampicillin resistance on 2×YT ampicillin plates at 37° C. Plasmid DNA was isolated from several transformants, and analyzed for presence of the pulB/C insert by 0.8% agarose electrophoresis with TBE buffer. One plasmid was designated pMBin115 (pDG268Δneo-triple tandem promoter/pulB/C with pel 3', pel 5', and spc) (FIG. 15).

Example 6

Construction of pRB212 for Cloning and Expression of the pulB/C-linker-AMY1048 CBM in B. subtilis Plasmid pRB212 is an E. coli replicon containing the expression cassette comprising of the triple tandem promoter, aprH ribosome binding site, the Bacillus acidopullulyticus pullulanase (pulB/C) coding region, a proline rich linker (-PEPTPEPN-), the A. contaminans α-amylase CBM (AMY1048 CBM) (CBM20 family) and aprH terminator. This expression cassette and the spc gene are flanked on both sides by fragments of the Bacillus subtilis pectate lyase (pel)

gene, permitting insertion of the expression cassette and spc gene at the pel locus of the *Bacillus subtilis* chromosome by double homologous recombination via the two pel fragments. The construction of pRB212 is described below.

Plasmid pRB210. A SOE (Splicing by Overlap Extension) strategy was devised to introduce a proline rich linker (-PEPTPEPN-) and AMY1048 CBM downstream of pulB/C. This SOE strategy allows for removal of pulB/C's stop codon, and insertion of the linker and AMY1048 CBM at the 3' end of pulB/C.

The Upstream Fragment:

The upstream fragment (3'-end of pulB/C) was PCR amplified from pMBin115 using primers that include an overhang homologous to the 5'-end of the downstream fragment. Primers 999448 and 060179 (SEQ ID NO: 8 and 9) were synthesized for polymerase chain reaction (PCR) amplification of a 571 bp upstream fragment. Nucleotides 1-10 of 060179 were added in order to complement the 5' end of the 060180 primer used to amplify the downstream fragment. These primers allow for the PCR amplification of the 3' end of pulB/C, not including pulB/C's stop codon.

This PCR was performed under the conditions described above.

The Downstream Fragment:

The downstream fragment (*A. contaminans* AMY1048 CBM (CBM20 family)) was PCR amplified from the cloned gene of AMY 1048 (SEQ ID NO: 1 in WO 2006/066596A2) using primers which include the -PEPTPEPTN- (SEQ ID NO: 1) linker and overhang homologous to the 3'-end of pulB/C. Primers 060180 and 999451 (SEQ ID NO: 10 and 11) were synthesized for polymerase chain reaction (PCR) amplification of a 542 bp downstream fragment: Nucleotides 1-24 of 060180 were added in order to introduce the linker -PEPTPEPN- (SEQ ID NO: 1) and complement the 5' end of the 060179 primer used to amplify the upstream fragment. Nucleotides 1-10 of 060180 represent the region of overlap between the upstream and downstream fragments.

This PCR was performed under the conditions described above.

The Full-Length Fragment:

The full length fragment was PCR amplified using as templates the upstream and downstream fragments described above. This PCR was performed using the primer pair 999448/999451 under the conditions described above.

This SOE provided a 1103 bp fragment which contains 561 bp of 3'-pulB/C, a 24 bp linker, and 518 bp comprising of AMY1048 CBM and downstream sequence.

This resulting PCR product of approximately 1103 bp was gel purified and cloned into vector pCR2.1 using a TOPO® TA PCR Cloning Kit for Sequencing and transformed into One Shot® TOP10 Chemically Competent *E. coli* cells according to the manufacturer's instructions. Plasmid DNA was isolated from one transformant and confirmed by digestions with Eco RI followed by 0.8% agarose electrophoresis with TBE buffer, which yielded expected fragments of approximately 3931 bp and 1121 bp. The DNA sequence of the cloned PCR fragment was confirmed by DNA sequencing. This plasmid was designated pRB210. The complete DNA sequence 3'-pulB/C-linker-AMY1048 CBM cloned in pCR2.1 is shown in SEQ ID NO: 12.

Figure 16:
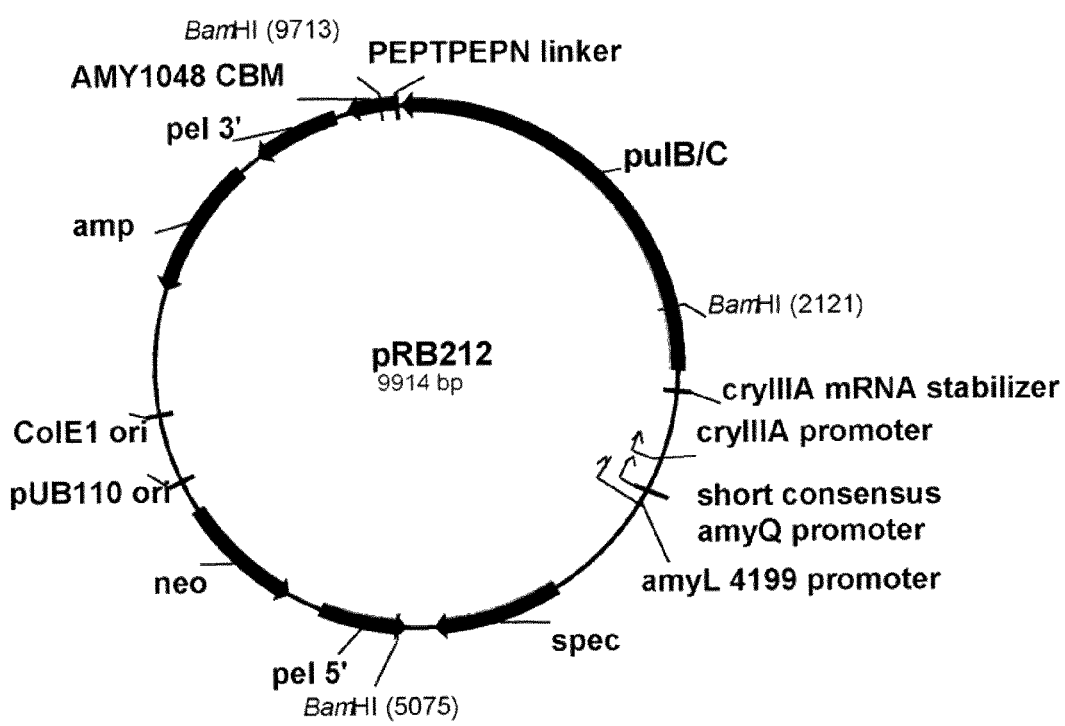

Plasmid pRB212. Plasmid pRB210 (pCR2.1-3'-pulB/C-linker-AMY1048 CBM) was digested with BstxX II and Mlu I, analyzed by 0.8% agarose electrophoresis with TBE buffer and a fragment of approximately 402 bp, bearing the 3'-pulB/C-linker-AMY1048 CBM, was purified using a QIAquick Gel Extraction Kit. Plasmid pMBin115 (pDG268Δneo-triple tandem promoter/pulB/C with pel 3', pel 5', and spc) was digested with BstxX II and Mlu I, analyzed by 0.8% agarose electrophoresis with TBE buffer, and a vector fragment of approximately 9442 bp was purified using a QIAquick Gel Extraction Kit. The pMBin115 vector fragment and 3'-pulB/C-linker-AMY 1048 CBM fragment were ligated as described above, and *E. coli* SURE cells were transformed with the ligation as described above, selecting for ampicillin resistance on 2×YT ampicillin plates at 37° C. Plasmid DNA was purified from several transformants using a QIAGEN robot according to the manufacturer's instructions and analyzed by Bam HI digestion on a 0.8% agarose gel using 0.5×TBE buffer. A plasmid was identified which contained the desired fragments (4638 bp, 2954 bp, and 2322 bp) was designated pRB212 (FIG. 16). This cloning strategy placed the linker and AMY 1048 CBM between pulB/C and a stop codon followed by aprH terminator. The pulB/C-linker-AMY1048 CBM coding region in this plasmid was confirmed to be error-free by DNA sequencing.

Example 7

Cloning and Expression of the pulB/C-linker-AMY1048 CBM in *B. subtilis*

Strain RB272. Plasmid pRB212 was used to transform *B. subtilis* 168Δ4 to spectinomycin resistance as described above. Integrants were screened for neomycin sensitivity, indicating double-crossover integration at the pel locus. The presence of the pulB/C expression cassette was confirmed by formation of clearing zones on a pullulan-azure overlay (and AZCL-pullulan overlay) as described above. One such integrant was designated RB268. Genomic DNA was isolated from *Bacillus subtilis* RB268.

Expression of pulB/C-linker-AMY 1048 CBM was effected in a protease-deficient host, A164Δ10 in order to minimize the processing and degradation of extracellular proteins (e.g. pulC-linker-CBM). To do so, the triple tandem promoter-pulB/C-linker-AMY1048 CBM expression cassette was then transferred to *B. subtilis* production host A164Δ10 by transformation of the host with RB268 genomic DNA to spectinomycin resistance. The presence of the pulB/C expression cassette was confirmed by formation of clearing zones on a pullulan-azure overlay (and AZCL-pullulan overlay) as described above. One such integrant was designated RB272, which contains the triple tandem promoter/pulB/C-linker-AMY1048 CBM expression cassette inserted at the pel locus of A164Δ10.

Control Strain RB265

The control strain RB265 is the A164Δ10 *Bacillus subtilis* host containing the expression cassette comprising the triple tandem promoter, aprH ribosome binding site, pullulanase (pulB/C) coding region, and aprH terminator integrated in single copy at the pel chromosomal locus.

pMBin115 was used to transform *B. subtilis* 168Δ4 to spectinomycin resistance. Integrants were screened for neomycin sensitivity, indicating double-crossover integration at the pel locus. The presence of the pulB/C expression cassette was confirmed by formation of clearing zones on a pullulan-azure overlay (and AZCL-pullulan overlay) as described above. One such integrant was designated 168Δ4::triple tandem promoter/pulB/C. Genomic DNA was isolated from *Bacillus subtilis* 168Δ4::triple tandem promoter/pulB/C.

The triple tandem promoter-pulB/C expression cassette was then transferred to *B. subtilis* production host A164Δ10 (Connelly et al., supra) by transformation of the host with 168Δ4::triple tandem promoter/pulB/C genomic DNA to spectinomycin resistance. The presence of the pulB/C expression cassette was confirmed by formation of clearing zones on a pullulan-azure overlay (and AZCL-pullulan overlay) as described above. The clearing zones produced by RB272 are slightly smaller than the clearing zones produced by the control strain RB265 harboring pulB/C without the AMY1048 CBM.

One such integrant was designated RB265, which contains the triple tandem promoter/pulB/C expression cassette inserted at the pel locus of A164Δ10.

Example 8

Fermentation for expression of pulB/C-linker-AMY 1048 CBM In *B. subtilis* A164Δ10

The strains RB265 and RB272 were tested in laboratory-scale fermentation as described below.
Seed Propagation Seeds were propagated on solid media and then transferred to shake flasks to make the final inocula. Strains were streaked from −80° C. freezer stocks onto SSB-4 plates.

Following this, plates were incubated at 37° C. for 20 hours and then transferred to another SSB-4 plate for an additional 20 hour incubation. They were then harvested with 5 mL of M9 buffer to create a bacterial suspension. This M9 suspension was then read at 650 nm and inoculation volume into 100 mL PRK50 baffled shake flasks was determined using the formula v=0.1/Abs650. Shake flasks incubated for 20 hours at 37° C. and 250 rpm.

Tanks containing DK Pullulanase media were inoculated by adding 100 mL of the appropriate shake flask culture to the tank for a total working volume of 1.0 L. Process control was achieved manually and through the use of FermWorks control and data logging software (Jova Solutions, San Francisco, Calif., USA).

Tanks were fed according to the profile with a sucrose feed and 4N $NH_4OH$/5M $H_3PO_4$ to control pH. Tanks were sparged with compressed air at a controlled rate using an electronic mass flow device. Agitation was standardized through calibrated motor controllers manually adjusted throughout the fermentation. Temperature was controlled using a 10° C. cold-finger and an electric heater probe.

Process control was monitored throughout the fermentation using the data logging feature on the FermWorks software package. These data were exported in the form of points taken every five minutes.

$pH_{high}$ was 6.8 at time 0, and 6.2 at time 20-24-48. $pH_{low}$ was 5.9 at time 0-20-24-48. The set point for the airp profile was kept at 2.25 L/m, and the set point for the temp profile was kept at 37. The set point for the RPM profile was 700 at time 0 and 1500 at time 1-3-48. The set point for the feed profile was 4.5 g/m at time 0; 22.5 g/m at time 15; 22.58 g/m at time 30; and 10.8 g/m a<t time 60.
Sampling Small samples for verification of online pH were taken at various times throughout the fermentation. Samples for storage/analysis were drawn from tanks at approximately 3, 24 and 48 hours. For assay analysis 200 micro-L of whole broth was loaded into a 96-well plate and frozen at −20° C. For future reference and the potential need to re-assay, 1 mL of whole broth was pipetted into each of two 1.7 mL Eppendorf tubes. These were stored at −20° C. in the whole broth library. An additional set of tubes was reserved for protein gel electrophoresis.

Example 9

Automated Pullulanase Assay

This method is used in conjunction with a Beckman Coulter Biomek NX (Beckman Coulter, Fullerton Calif.). Culture supernatants were diluted appropriately in 0.1M sodium acetate buffer pH 5.0 (sample buffer). Pullulanase standard was diluted using 2-fold steps starting with a 2 NPUN/ml concentration and ending with a 0.031 NPUN/ml concentration in the sample buffer. A total of 75 μl of each dilution including standard was transferred to a 96-well flat bottom plate (assay plate). Forty micro-liters of a 2.5% Red-pullulan substrate (Megazymes International Ireland Ltd., Wicklow, Ireland) in sample buffer was added to each well. The assay plate was then incubated at 40° C. for 10 minutes. Upon completion of the incubation period 190 μl of ethanol (95% v/v) was added per well followed with an ambient incubation for 10 minutes. The assay was then centrifuged at 3,000 RPM for 10 minutes. One-hundred-fifty micro-liters of supernatant was then removed and placed in a new 96-well flat bottom plate. An absorbance of 510 nm was then measured. Sample concentrations were determined by extrapolation from the generated standard curve.

Approximate pullulanase titers for RB272 and RB265 were estimated to be in the multi-gram per liter range.

Example 10

SDS-PAGE Analyses of RB272 and RB265 Fermentation Samples

In order to test the stability of the fusion, fermentation samples of RB265 and RB272 were ran on a 7.5% Tris-HCl SDS-PAGE (Bio-Rad Laboratories, CA, USA) according to the manufacturer's instructions. Such analysis showed that the major protein product were of the expected size for mature PulB/C (~91.7 kDa) and for the fusion pulB/C-linker-AMY1048 CBM (~103 kDa). Such an analysis not only confirmed that the strain RB272 produces a stable fusion, but also confirmed the high yield of such a fusion at 24 h.

Example 11

Conversion of Granular Wheat Starch into Glucose

This example illustrates the conversion of granular starch into glucose using a pullulanase with or without a CBM20 in combination with a glucoamylase.

Initially a slurry with 10% wheat starch was made by adding 10 gram wheat starch to 90 mL of 0.2 M Na-acetate pH 5.5 under continuous stirring.

The following enzymes were dosed at time point zero (Table 1).

TABLE 1

| | Enzyme dosing | | |
|---|---|---|---|
| Treatment | AMG dosage AGU/g DS | Pullulanase dosage NPUN/g DS | Pullulanase + CBM dosage NPUN/g DS |
| AMG | 0.2 | | |
| AMG + Pullulanase | 0.2 | 0.32 | |
| AMG + Pullulanase + CBM | 0.2 | | 0.32 |

After addition of the enzymes, the starch slurries were incubated at 60° C. At time point 25 and 50 hours aliquots were removed and the amount of glucose in solution was determined. The glucose content was determined by measuring the reducing ends relative to a glucose standard curve.

The results are shown in Table 2 below.

TABLE 2

Results obtained after 25 and 50 hours hydrolysis

| Time (hours) | mg glucose released/mL | | |
|---|---|---|---|
| | AMG | AMG + Pullulanase | AMG + Pullulanase + CBM |
| 25 | 39 | 54 | 66 |
| 50 | 43 | 57 | 67 |

Example 12

Conversion of Granular Corn Starch into Glucose

This example Illustrates the conversion of granular starch into glucose using a pullulanase with or without a CBM20 in combination with a glucoamylase.

Initially a slurry with 3.2% corn starch was made by adding 3.6 gram corn starch to 112 mL of 50 mM Na-acetate, 1 mM $CaCl_2$ under continuous stirring. The pH was adjusted to 4.0 with acetic acid.

The following enzymes were dosed at time point zero (Table 3).

TABLE 3

Enzyme dosing

| Treatment | AMG dosage AGU/g DS | Pullulanase dosage NPUN/g DS | Pullulanase + CBM dosage NPUN/g DS |
|---|---|---|---|
| AMG | 0.3 | | |
| AMG + Pullulanase | 0.3 | 10 | |
| AMG + Pullulanase + CBM | 0.3 | | 10 |

After addition of the enzymes the starch slurries were placed in a water batch at 32° C. At time point 21 and 45 hours aliquots were removed and the amount of glucose in the solutions was determined as described above.

The results obtained are shown in Table 4 below.

| Time (hours) | mg glucose released/mL | | |
|---|---|---|---|
| | AMG | AMG + Pullulanase | AMG + Pullulanase + CBM |
| 21 | 3.39 | 3.84 | 4.24 |
| 45 | 5.39 | 5.84 | 6.25 |

The invention claimed is:

1. An isolated polypeptide having pullulanase activity, comprising a catalytic domain and a starch binding domain, wherein the catalytic domain comprises the sequence of the amino acids numbered 1-829 of SEQ ID NO: 14.

2. The polypeptide of claim 1, wherein the starch binding domain belongs to a family selected from the group consisting of CBM-20, CBM-21, CBM-25, CBM-26, CBM-34, CBM-41 and CBM-45.

3. The polypeptide of claim 2, wherein the starch binding domain belongs to CBM-20.

4. The polypeptide of claim 3, wherein the starch binding domain is the starch binding domain of an *Anoxybacillus contaminans* alpha-amylase or the starch binding domain of a *Thermoanaerobacter* sp. CGTase.

5. The polypeptide of claim 1, wherein the starch binding domain comprises the sequence of the amino acids numbered 838-936 of SEQ ID NO: 14.

6. The polypeptide of claim 1, further comprising a linker connecting the catalytic domain and the starch binding domain.

7. The polypeptide of claim 6, wherein the linker consists of less than 100 amino acids.

8. The polypeptide of claim 7, wherein the linker is proline rich.

9. The polypeptide of claim 8, where the linker is PEPTPEPN.

10. A method for raw starch degradation comprising incubating non-gelatinized starch and water with the polypeptide of claim 1.

11. The method of claim 10 comprising:
    (a) providing a mixture comprising raw starch and water;
    (b) adding the polypeptide together with an endo-acting amylase or an exo-acting amylase; and
    (c) incubating the mixture at a temperature and for a time which are effective to degrade the starch.

12. The method of claim 11, wherein the exo-acting amylase is a glucoamylase.

13. An isolated polypeptide, comprising the amino acid sequence of SEQ ID NO: 13.

14. A method for raw starch degradation comprising incubating non-gelatinized starch and water with the polypeptide of claim 13.

15. The method of claim 14 comprising:
    (a) providing a mixture comprising raw starch and water;
    (b) adding the polypeptide together with an endo-acting amylase or an exo-acting amylase; and
    (c) incubating the mixture at a temperature and for a time which are effective to degrade the starch.

16. The method of claim 15, wherein the exo-acting amylase is a glucoamylase.

* * * * *